United States Patent
Chiba

(10) Patent No.: US 11,885,954 B2
(45) Date of Patent: Jan. 30, 2024

(54) ENDOSCOPE SYSTEM

(71) Applicant: HOYA CORPORATION, Tokyo (JP)

(72) Inventor: Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 23 days.

(21) Appl. No.: 17/048,425

(22) PCT Filed: Aug. 30, 2019

(86) PCT No.: PCT/JP2019/034087
§ 371 (c)(1),
(2) Date: Oct. 16, 2020

(87) PCT Pub. No.: WO2020/045619
PCT Pub. Date: Mar. 5, 2020

(65) Prior Publication Data
US 2021/0228068 A1    Jul. 29, 2021

(30) Foreign Application Priority Data

Aug. 31, 2018  (JP) .................. 2018-163667

(51) Int. Cl.
  *G02B 23/24*    (2006.01)
  *A61B 1/00*     (2006.01)
  (Continued)

(52) U.S. Cl.
  CPC ...... *G02B 23/2469* (2013.01); *A61B 1/00043* (2013.01); *A61B 1/000094* (2022.02);
  (Continued)

(58) Field of Classification Search
  CPC .......... A61B 1/00009; A61B 1/000094; A61B 1/00043; A61B 1/04; A61B 1/044;
  (Continued)

(56) References Cited

U.S. PATENT DOCUMENTS 10,426,325 B2  10/2019 Chiba
11,224,335 B2   1/2022 Chiba
              (Continued)

FOREIGN PATENT DOCUMENTS

CN    105380587 A    3/2016
JP    03-080834      4/1991
              (Continued)

OTHER PUBLICATIONS

Official Communication issued in International Bureau of WIPO Patent Application No. PCT/JP2019/034087, dated Nov. 19, 2019.
(Continued)

*Primary Examiner* — Aaron B Fairchild
*Assistant Examiner* — Julianna J Nicolaus
(74) *Attorney, Agent, or Firm* — GREENBLUM & BERNSTEIN, P.L.C.

(57) ABSTRACT

Provided is a technology capable of generating and presenting more kinds of special light images with higher image quality. An endoscope system according to the present disclosure performs image processing using a G1 image data (image data obtained by irradiating light of 524±3 nm to 582±3 nm) and at least one of R1 image (image data obtained by irradiating light of 630±3 nm to 700±3 nm) data other than the G1 image data, B1 image data (452±3 nm to 502±3 nm), R2 image data (image data obtained by irradiating light of 582±3 nm to 630±3 nm), G2 image data (image data obtained by irradiating light of 502±3 nm to 524±3 nm), and B2 image data (image data obtained by irradiating light of 420±3 nm to 452±3 nm) so as to generate a special light image (FIG. 7).

7 Claims, 19 Drawing Sheets

(51) Int. Cl.
*A61B 1/05* (2006.01)
*A61B 1/06* (2006.01)
*A61B 1/07* (2006.01)
*A61B 1/04* (2006.01)

(52) U.S. Cl.
CPC ............. *A61B 1/044* (2022.02); *A61B 1/05* (2013.01); *A61B 1/0646* (2013.01); *A61B 1/0655* (2022.02); *A61B 1/07* (2013.01)

(58) Field of Classification Search
CPC ....... A61B 1/05; A61B 1/0638; A61B 1/0646; A61B 5/1032; A61B 5/489; G06T 2207/10024; G06T 2207/10028; G06T 2207/10068; G06T 2207/30101
See application file for complete search history.

(56) References Cited

U.S. PATENT DOCUMENTS

| | | | |
|---|---|---|---|
| 2005/0014995 A1* | 1/2005 | Amundson | A61B 90/36 600/105 |
| 2011/0245642 A1* | 10/2011 | Minetoma | A61B 1/0655 600/324 |
| 2012/0010465 A1* | 1/2012 | Erikawa | A61B 1/0653 600/109 |
| 2012/0157768 A1 | 6/2012 | Saito | |
| 2012/0241620 A1 | 9/2012 | On | |
| 2012/0327205 A1 | 12/2012 | Takahashi | |
| 2016/0058274 A1 | 3/2016 | Chiba | |
| 2016/0120449 A1* | 5/2016 | Chiba | A61B 1/0638 600/311 |
| 2016/0287061 A1* | 10/2016 | Shigeta | A61B 1/000094 |
| 2018/0000334 A1 | 1/2018 | Morishita | |
| 2018/0000335 A1* | 1/2018 | Igarashi | A61B 1/000094 |
| 2018/0064320 A1 | 3/2018 | Chiba | |
| 2018/0279853 A1* | 10/2018 | Daidoji | A61B 1/0669 |
| 2019/0069768 A1 | 3/2019 | Chiba | |
| 2019/0069825 A1* | 3/2019 | Wada | A61B 5/02007 |
| 2019/0125229 A1 | 5/2019 | Obara et al. | |
| 2019/0170647 A1 | 6/2019 | Ikenaga et al. | |

FOREIGN PATENT DOCUMENTS

| | | |
|---|---|---|
| JP | 2005-507731 | 3/2005 |
| JP | 2005-507731 A | 3/2005 |
| JP | 2011-125404 | 6/2011 |
| JP | 2011-125404 A | 6/2011 |
| JP | 2011-135983 | 7/2011 |
| JP | 2011-135983 A | 7/2011 |
| JP | 2011-200330 | 10/2011 |
| JP | 2012-016545 | 1/2012 |
| JP | 2012-016545 A | 1/2012 |
| JP | 2013-063097 | 4/2013 |
| JP | 2013-063097 A | 4/2013 |
| JP | 2013-078460 A | 5/2013 |
| JP | 5303012 | 6/2013 |
| JP | 5303012 B2 | 6/2013 |
| JP | 2014-061152 | 4/2014 |
| JP | 2014-061152 A | 4/2014 |
| JP | 2015-177812 A | 10/2015 |
| JP | 2016-022043 A | 2/2016 |
| JP | 2016022043 A * | 2/2016 |
| JP | 2017-508579 A | 3/2017 |
| JP | 2017-148392 | 8/2017 |
| JP | 2017-148392 A | 8/2017 |
| JP | 2018-000616 | 1/2018 |
| JP | 2018-000616 A | 1/2018 |
| JP | 2018-027272 | 2/2018 |
| JP | 2018-027272 A | 2/2018 |
| WO | 2016/151672 | 9/2016 |
| WO | 2017/051455 | 3/2017 |
| WO | 2017/051779 | 3/2017 |
| WO | WO2018/083888 A1 | 5/2018 |

OTHER PUBLICATIONS

Office Action issued in Chinese patent application No. 201980026603.X, dated May 31, 2023.

* cited by examiner

FIG. 9
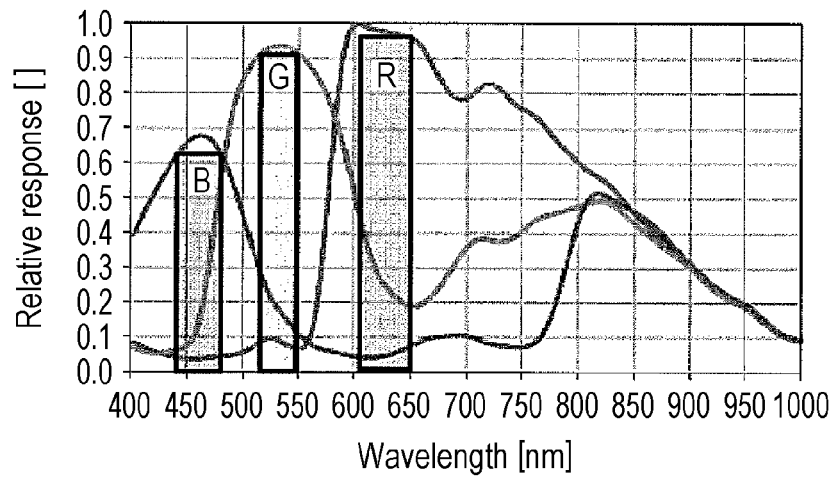
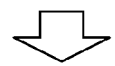
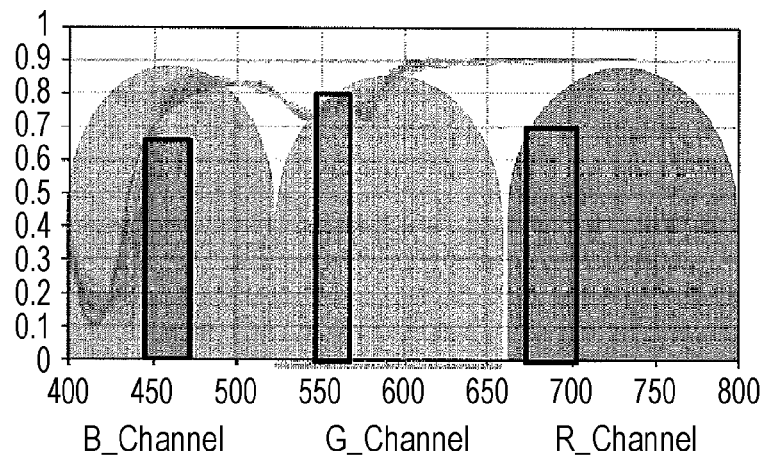

FIG. 12
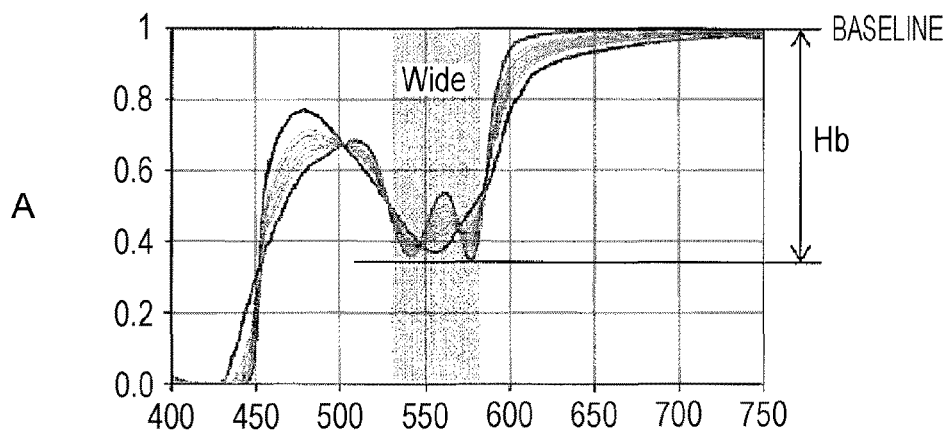
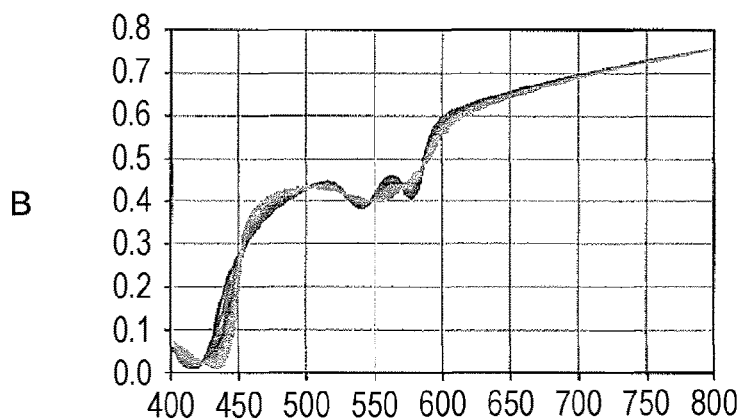
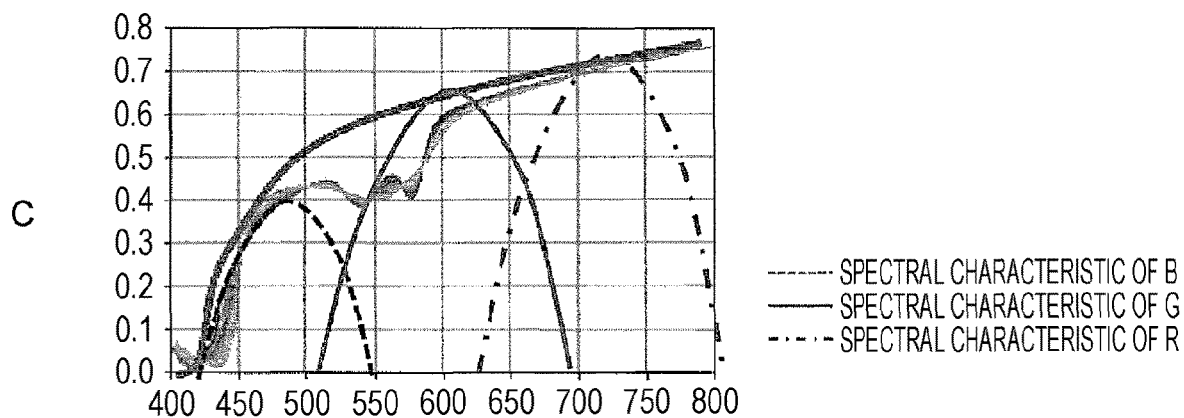

FIG. 13 A    G1/G3
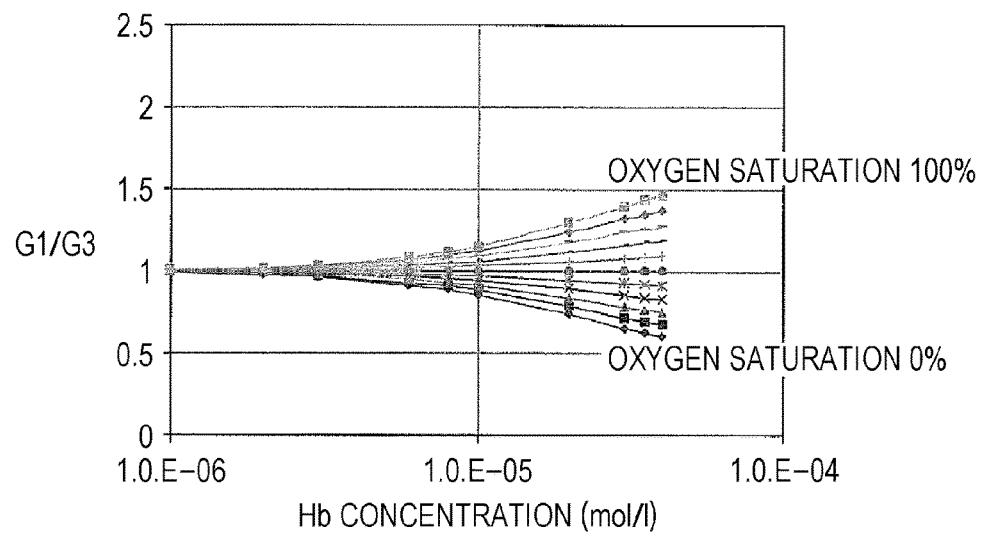
FIG. 13 B    B1/G1
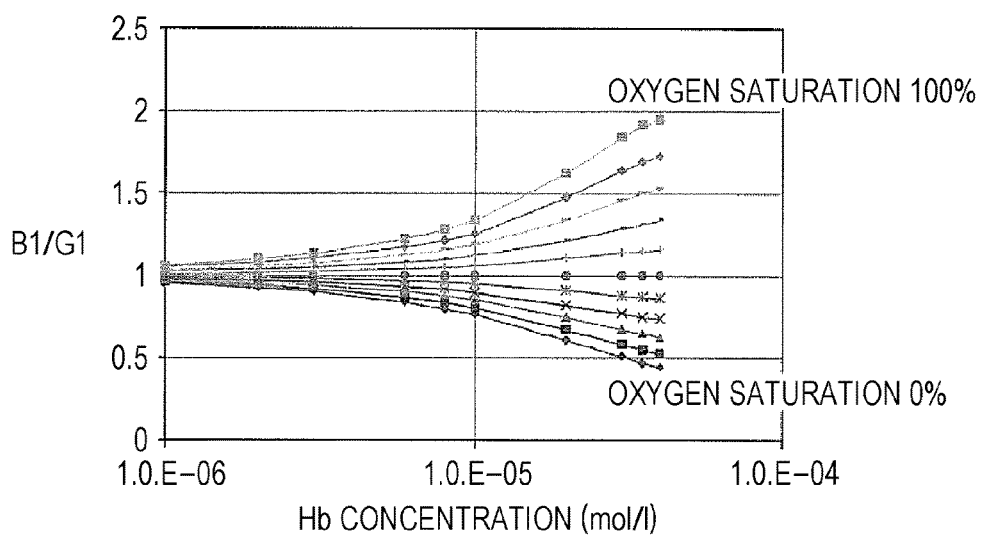

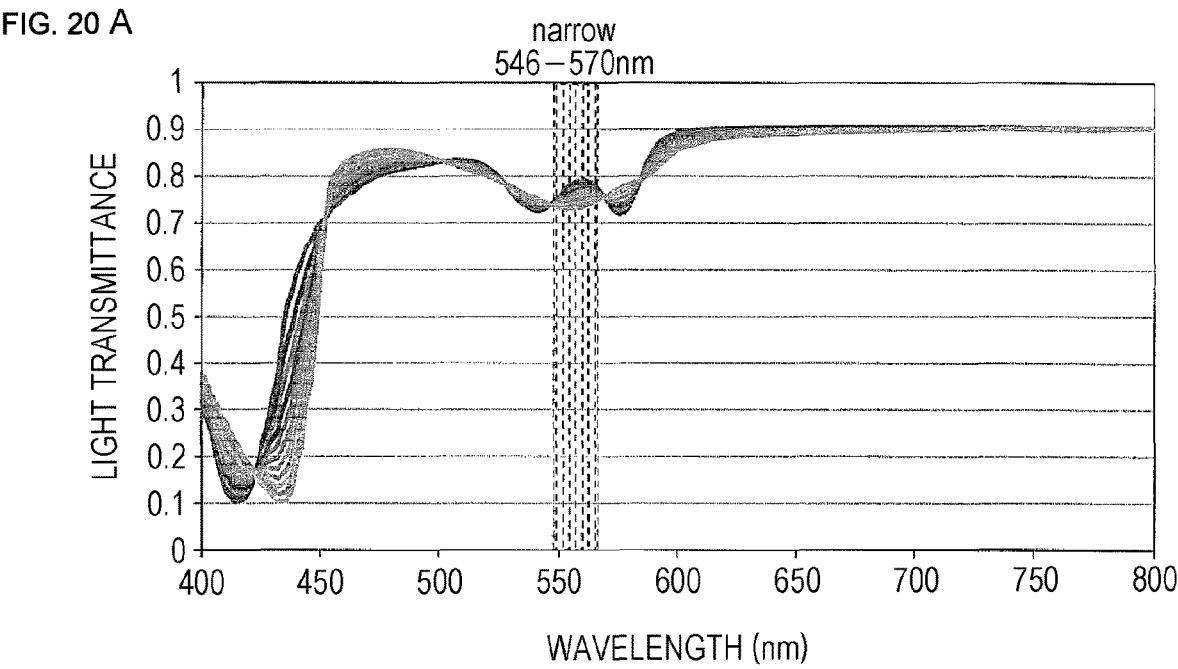
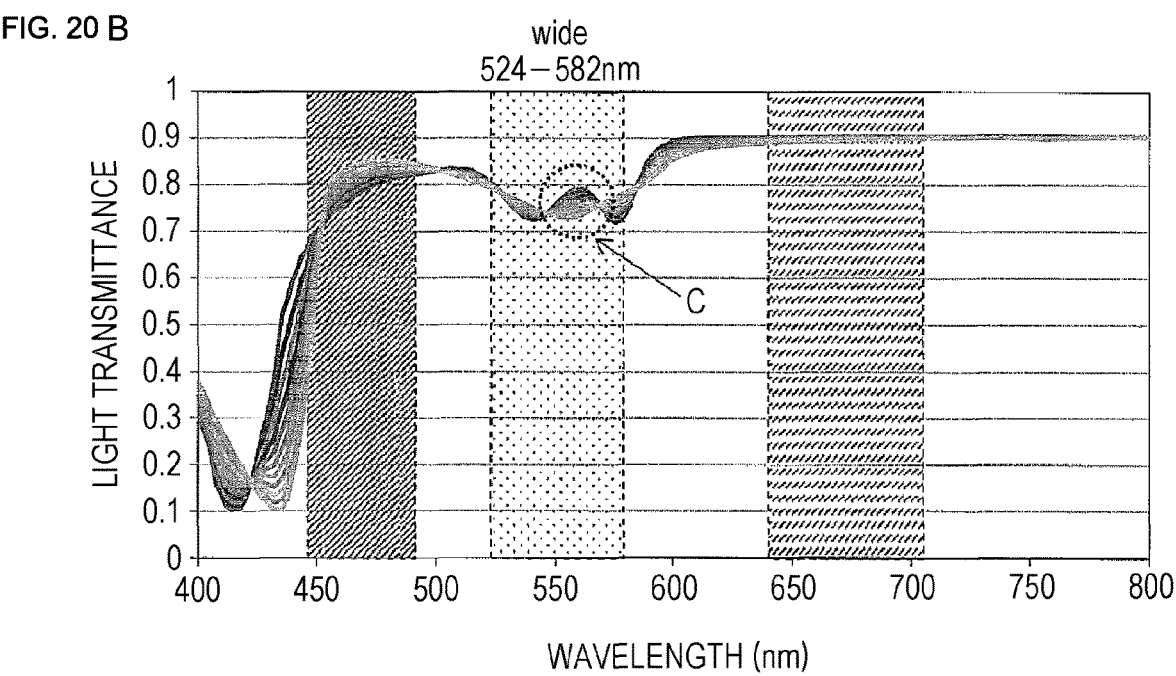

ENDOSCOPE SYSTEM

TECHNICAL FIELD

The present disclosure relates to an endoscope system and a method for operating the endoscope system.

BACKGROUND ART

By using an endoscope device (spectroscopic endoscope device) having a spectral image capturing function, it is possible to obtain information (for example, a reflection spectrum) regarding the spectral characteristics of biological tissues such as mucous membranes of a digestive organ. It is known that the reflection spectrum of the biological tissue reflects information on the type and concentration of the substance contained in the vicinity of the surface layer of the biological tissue to be measured. Specifically, it is known that the absorption calculated from the reflection spectrum of the biological tissue is a linear superposition of the absorptions of a plurality of substances forming the biological tissue.

Further, it is known that the biological tissue of a lesioned part is different from the biological tissue of a healthy part in the composition and the amount of components. In particular, it has been reported in many previous studies that abnormalities in lesions represented by cancer are deeply related to blood conditions, in particular, total blood volume and oxygen saturation. Here, qualitatively and quantitatively observing two biological tissues of interest using the spectroscopic characteristic amount in the visible region is a technique that is often used in the field of spectroscopic chemistry. Therefore, it is possible to estimate whether the biological tissue contains any lesion by comparing the spectral characteristics of the blood of the biological tissue including the lesion with that of the biological tissue containing only the healthy portion.

Regarding the above-mentioned spectroscopic endoscope device, for example, Patent Literature 1 discloses "To perform a plurality of types of special light observation with a simple configuration, a living body observation device (1) is provided which includes an illumination unit (3, 7) that irradiates a biological tissue with illumination light containing light of a region of each of R, G, and B, an imaging unit (8) that acquires an image signal from reflected light in the biological tissue (X) of the illumination light, a narrowband light generation unit (F1, F2) that are arranged in the illumination unit (3, 7) or the imaging unit (8) and generates light of two narrow bandwidths on both sides interposing the center wavelength of the wavelength band in at least one wavelength band of R, G, and B of the illumination light in the wavelength band of the illumination light, and an image generation unit (18) that generates an image based on two or more image signals obtained by the imaging unit (8) that acquires reflected light of two or more narrow bandwidths" (Abstract).

CITATION LIST

Patent Literature

Patent Literature 1: WO 2016/151672

SUMMARY OF INVENTION

Technical Problem

In recent years, in the spectroscopic endoscope device, it is desired to generate and observe more kinds of special light images in order to support various usage modes.

However, according to the spectroscopic endoscope device of Patent Literature 1, in addition to the normal image, only three types of special light images are generated, which does not meet the recent need to observe more types of special light images. It is also desired to generate a high quality special light image.

The present disclosure has been made in view of such circumstances, and provides a technique that enables to generate and present more types of special light images with higher image quality.

Solution to Problem

In order to solve the above problems, an endoscope system according to this embodiment is provided which is capable of operating in a normal observation mode for irradiating a biological tissue with white light to acquire an image and a special observation mode for irradiating a biological tissue with light of a specific wavelength band to acquire an image. The endoscope system includes an illumination unit that irradiates a biological tissue with illumination light including at least R of a first wavelength band, G of a second wavelength band, B of a third wavelength band, R of a fourth wavelength band, G of a fifth wavelength band, and B of a sixth wavelength band, an imaging unit that generates image data based on reflected light from the biological tissue generated by irradiating the biological tissue with the illumination light, an image processing unit that acquires the image data from the imaging unit and performs a predetermined image process, and a display unit that displays an image generated by the predetermined image process of the image processing unit on a screen. At least the second wavelength band, the third wavelength band, the fifth wavelength band, and the sixth wavelength band are defined with boundaries therebetween by a wavelength at an isosbestic point at which transmittance becomes constant regardless of oxygen saturation. The second wavelength band includes within the band an isosbestic point other than the isosbestic point which is the boundary of the band, the sixth wavelength band is a shorter wavelength band than the third wavelength band, the fifth wavelength band is a shorter wavelength band than the second wavelength band, the fourth wavelength band is a shorter wavelength band than the first wavelength band. The image data includes R1 image data corresponding to R light of the first wavelength band, G1 image data corresponding to G light of the second wavelength band, B1 image data corresponding to B light of the third wavelength band, R2 image data corresponding to R light of the fourth wavelength band, G2 image data corresponding to G light of the fifth wavelength band, and B2 image data corresponding to B light of the sixth wavelength band. The image processing unit generates a special light image by performing an image process using the G1 image data and at least one of the R1 image data, the B1 image data, the R2 image data, the G2 image data, and the B2 image data other than the G1 image data.

Further features related to the present disclosure will become apparent from the description of the present specification and the accompanying drawings. The present disclosure is achieved and implemented by elements and combinations of various elements and by modes of the following detailed description and the appended claims.

It is to be understood that the description in this specification is merely exemplary and is not intended to limit the scope of the claims or the application in any way.

Advantageous Effects of Invention

According to the present disclosure, it is possible to generate and present more types of special light images with higher image quality.

BRIEF DESCRIPTION OF DRAWINGS

FIG. 9 is a diagram illustrating a process of performing a matrix conversion operation on an RGB value (upper part of FIG. 9: (Rs, Gs, Bs)) of an on-chip filter and generating a corrected RGB value (RGB_related_values).

FIG. 10A is a diagram illustrating an example of a visible light image of an observation site. FIG. 10B is a diagram illustrating a B2 image (an image obtained by irradiating light with a wavelength band of 420±3 nm to 452±3 nm), and illustrating an image example of the state of a blood vessel at a shallow portion from the observation site. FIG. 10C is a diagram illustrating a G1 image (an image obtained by irradiating light with a wavelength band 524±3 nm to 582±3 nm), and illustrating an image example of the state of a blood vessel at a medium depth from the observation site. FIG. 10D is a diagram illustrating an R1 image (an image obtained by irradiating light with a wavelength band of 630±3 nm to 700±3 nm), and illustrating an image example of the state of a blood vessel at a position deeper than the observation site.

FIG. 12 is a diagram for explaining the principle of obtaining a hemoglobin concentration (blood concentration) with the influence of scattered light removed.

FIGS. 13A and 13B are diagrams illustrating a conventional oxygen saturation calculation table example (FIG. 13A) and an oxygen saturation calculation table example (FIG. 13B) according to this embodiment.

FIG. 14A is a diagram illustrating an example of a visible light image of the observation site. FIG. 14B is a diagram illustrating an image example of a site where the blood concentration (Hb concentration) is equal to or higher than a predetermined Hb value (a site with a large blood flow) in the observation site. FIG. 14C is a diagram illustrating an image example of a site where the oxygen saturation is equal to or lower than a predetermined percentage (a site where the oxygen consumption is large) in the observation site. FIG. 14D is a diagram illustrating an image example of a site where the blood concentration (Hb concentration) is equal to or higher than a predetermined Hb value and the oxygen saturation is equal to or lower than a predetermined % (a site where the blood flow is large but the oxygen amount is low) in the observation site.

FIG. 16A is a diagram illustrating an image example of a normal RGB output of the observation site. FIG. 16B is a diagram illustrating an example of the blood transparentized image when a subtraction parameter of the G1 image is set (for example, the subtraction parameter can be set to −0.2). FIG. 16C is a diagram illustrating an example of the blood transparentized image when the subtraction parameter of the G1 image is set to 0. FIG. 16D is a diagram illustrating an example of the blood transparentized image when the subtraction parameter of the G1 image is set to be larger (for example, the subtraction parameter can be set to −0.5).

FIGS. 20A and 20B are diagrams illustrating the third optical filter (FIG. 20A: corresponding to the optical filter illustrated in FIG. 4) for acquiring a narrowband image (an image formed by light having a wavelength of 546±3 to 570±3 nm) and the first optical filter (FIG. 20B: corresponding to the optical filter illustrated in FIG. 2) for acquiring a wideband image (an image formed by light having a wavelength of 524±3 to 582±3 nm).

DESCRIPTION OF EMBODIMENTS

<Configuration of Endoscope System>

Figure 1:
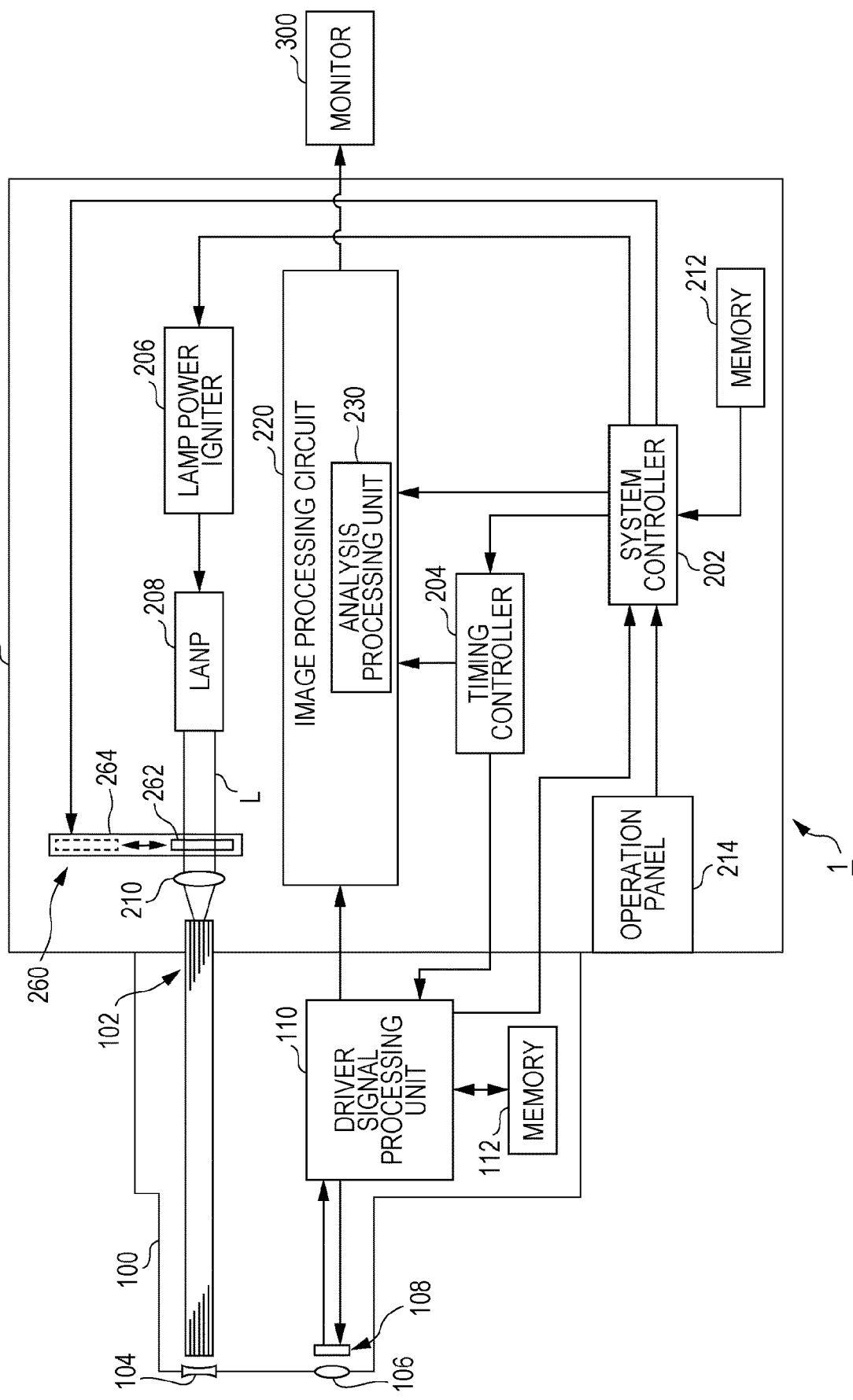
FIG. 1 is a diagram illustrating a schematic configuration example of an endoscope system 1 according to the embodiment.

FIG. 1 is a diagram illustrating a schematic configuration example of an endoscope system 1 according to this embodiment. As illustrated in FIG. 1, the endoscope system 1 includes an electronic scope (endoscope device) 100, a processor 200, and a monitor 300.

The processor 200 includes a system controller 202, a timing controller 204, an image processing unit 220, a lamp 208, and an optical filter device 260. The system controller 202 executes various programs stored in a memory 212 and integrally controls the entire endoscope system 1. The system controller 202 is connected to an operation panel 214. The system controller 202 changes each operation of the electronic endoscope system 1 and parameters for each operation in accordance with a user's instruction input by the operation panel 214. The timing controller 204 outputs a clock pulse for adjusting the operation timing of each unit to each processing unit in the electronic endoscope system 1.

The lamp 208 emits the irradiation light L after being activated by a lamp power igniter 206. The lamp 208 is, for example, a high-intensity lamp such as a xenon lamp, a halogen lamp, a mercury lamp, and a metal halide lamp, or an LED (Light Emitting Diode). The irradiation light L is light (or white light including at least the visible light region) having a spectrum that mainly spreads from the visible light region to the invisible infrared light region.

The optical filter device 260 is arranged between the lamp 208 and a condenser lens 210. The optical filter device 260 includes a filter drive unit 264 and an optical filter 262 mounted on the filter drive unit 264. The filter drive unit 264 is configured such that the optical filter 262 is slidable in a direction orthogonal to the optical path between the position on the optical path of the irradiation light L (solid line) and the position retracted from the optical path (broken line). Note that the configuration of the filter drive unit 264 is not limited to the above-described one, and the optical filter 262 may be inserted into and removed from the optical path of the irradiation light L by rotating the optical filter 262 around a rotation axis deviated from the center of gravity of the optical filter 262, for example, like a rotary filter device. Details of the optical filter 262 will be described later.

The endoscope system 1 of this embodiment is configured to operate in three operation modes: a normal observation mode in which the white light emitted from the lamp 208 is used as it is (or, after removing the infrared component and/or the ultraviolet component) as illumination light (normal light Ln) to perform the endoscope observation; a special observation mode in which a filtered light Lf obtained by passing white light through the optical filter 262 (or further removing infrared component and/or ultraviolet component) is used as illumination light; and a baseline measurement mode in which a correction value used in the special observation mode is acquired. The optical filter 262 is arranged at a position retracted from the optical path in the normal observation mode, and is arranged on the optical path in the special observation mode.

The irradiation light L (filtered light Lf or normal light Ln) that has passed through the optical filter device 260 is condensed by the condenser lens 210 on the incident end surface of the LCB (Light Carrying Bundle) 102 and introduced into the LCB 102.

The irradiation light L introduced into the LCB 102 is propagated in the LCB 102 and emitted from an exit end surface of the LCB 102 disposed at a distal end of the electronic scope 100, and irradiated to the object via a light distribution lens 104. Return light from the object irradiated with the irradiation light L forms an optical image on a light receiving surface of a solid-state image sensor 108 via an objective lens 106.

The solid-state image sensor 108 is, for example, a single-plate color CCD (Charge Coupled Device) image sensor having a Bayer pixel arrangement. The solid-state image sensor 108 accumulates the optical image formed on each pixel on the light receiving surface as electric charges according to the amount of light, and generates and outputs an image signal (image data). The solid-state image sensor 108 includes a so-called on-chip color filter in which an R filter that transmits red light, a G filter that transmits green light, and a B filter that transmits blue light are directly formed on each light receiving element of the solid-state image sensor 108. The image signal generated by the solid-state image sensor 108 includes the image signal R picked up by the light receiving element where the R filter is mounted, and the image signal G picked up by the light receiving element where the G filter is mounted, and the image signal B picked up by the light receiving element where the B filter is mounted.

Note that the solid-state image sensor 108 is not limited to a CCD image sensor, and may be replaced with a CMOS (Complementary Metal Oxide Semiconductor) image sensor or other types of imaging devices.

As illustrated in FIG. 1, the electronic scope 100 includes a driver signal processing unit 110 in a connection portion with the processor 200. An image signal is input to the driver signal processing unit 110 from the solid-state image sensor 108 in a field cycle. The driver signal processing unit 110 performs a predetermined process on the image signal input from the solid-state image sensor 108, and then outputs the image signal to the image processing unit 220 of the processor 200.

The driver signal processing unit 110 also accesses a memory 112 to read out specific information of the electronic scope 100. The specific information of the electronic scope 100 recorded in the memory 112 includes, for example, the number of pixels and sensitivity of the solid-state image sensor 108, an operable field rate, a model number, or the like. The driver signal processing unit 110 outputs the specific information read from the memory 112 to the system controller 202.

The system controller 202 performs various calculations based on the specific information of the electronic scope 100 and generates a control signal. The system controller 202 controls the operation and timing of various processing units in the processor 200 using the generated control signal so as to perform a process suitable for the electronic scope connected to the processor 200.

The timing controller 204 supplies a clock pulse to the driver signal processing unit 110 in accordance with timing control by the system controller 202. The driver signal processing unit 110 performs driving control of the solid-state image sensor 108 at a timing synchronized with the field rate of the video image processed on the processor 200 side in accordance with the clock pulse supplied from the timing controller 204.

The image processing unit 220 performs predetermined signal processing such as color complementation, matrix calculation, Y/C separation, and the like on the image signal input from the driver signal processing unit 110 in one field cycle, and then generates screen data for monitor display, and converts the generated screen data for monitor display into a predetermined video format signal. The converted video format signal is output to the monitor 300. With this processing, an image of the object is displayed on a display screen of the monitor 300.

The image processing unit 220 also includes the analysis processing unit 230. For example, in the special observation mode, the analysis processing unit 230 performs a spectroscopic analysis process based on the acquired image signals R (Red), G (Green), and B (Blue), calculates an index value having a correlation with an oxygen saturation in a biological tissue that is an object, and generates image data for visually displaying the calculated result. An example of the internal configuration of the analysis processing unit 230 will be described later (see FIG. 7).

As described above, the endoscope system 1 of this embodiment is configured to operate in three modes: without using the optical filter 262, the normal observation mode in which white light (normal light Ln) emitted from the lamp 208 is used as illumination light; the special observation mode in which the filtered light Lf obtained by passing white light through the optical filter 262 is used as illumination light to perform the spectroscopic analysis; and the baseline measurement mode to acquire a correction value for the special observation. Switching between the modes is performed by user's operation on the operation unit of the electronic scope 100 or the operation panel 214 of the processor 200.

In the normal observation mode, the system controller 202 controls the optical filter device 260 to retract the optical filter 262 from the optical path, and irradiates the object with the normal light Ln to perform imaging. Then, the image data captured by the image sensor 108 is subjected to image processing as needed, converted into a video signal, and displayed on the monitor 300.

In the special observation mode and the baseline measurement mode, the system controller 202 controls the optical filter device 260 to arrange the optical filter 262 on the optical path and irradiates the object with the filtered light Lf to perform imaging. Then, in the special observation mode, an analysis process (a depth-specific blood vessel running image generation process, a characteristic region identifying process, a blood transparentizing process, etc.) described below is performed based on the image data captured by the image sensor 108.

The baseline measurement mode is a mode for acquiring data for standardization processing of the special observation mode before performing the actual endoscopic observation, in which a color reference plate such as an achromatic diffuser plate or a standard reflection plate is taken as an object and imaging performs under the illumination of the filtered light Lf.

The image data R(x,y), G(x,y), and B(x,y) of the three primary colors captured using the filtered light Lf in the baseline measurement mode are respectively stored in the internal memory of the analysis processing unit 230 as the baseline image data BLR(x,y), BLG(x,y), and BLB(x,y). Note that R(x,y), G(x,y), B(x,y) and BLR(x,y), BLG(x,y), BLB(x,y) are respectively the values of the image data and baseline image data of the pixel (x,y). In addition, the pixel (x,y) is identified by the horizontal coordinate x and the vertical coordinate y.

<Configuration of Optical Filter (Band)>

Figure 2:
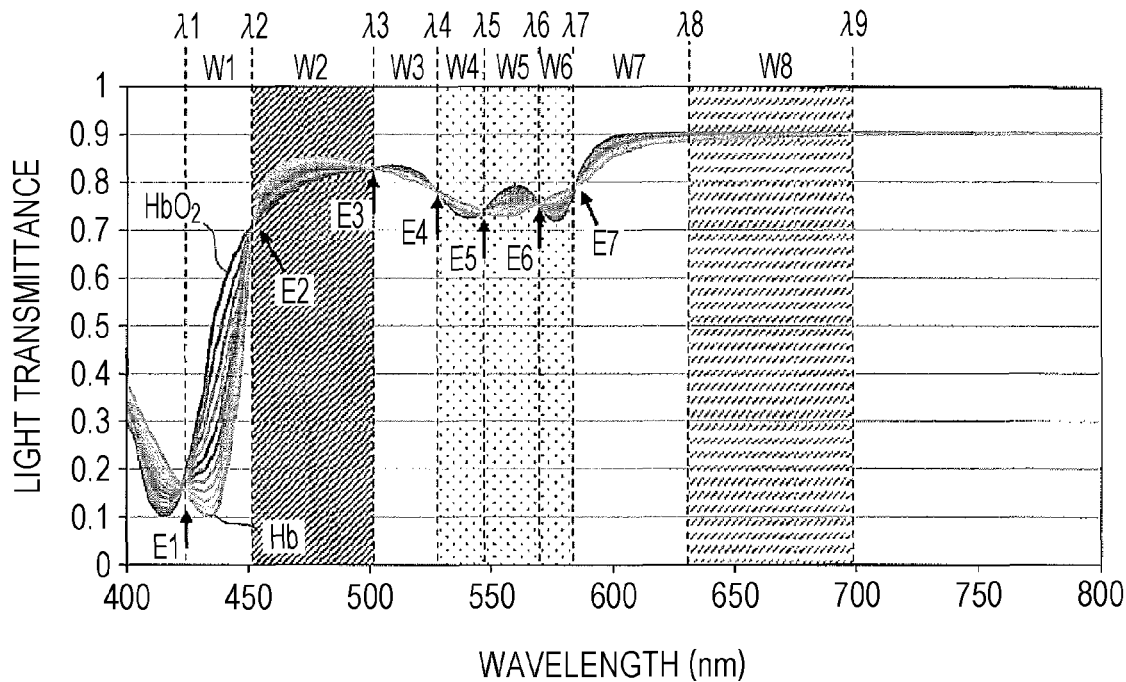
FIG. 2 is a diagram illustrating the spectral characteristics and the wavelength band of a first optical filter used when acquiring a wideband image (G1 image).
Figure 3:
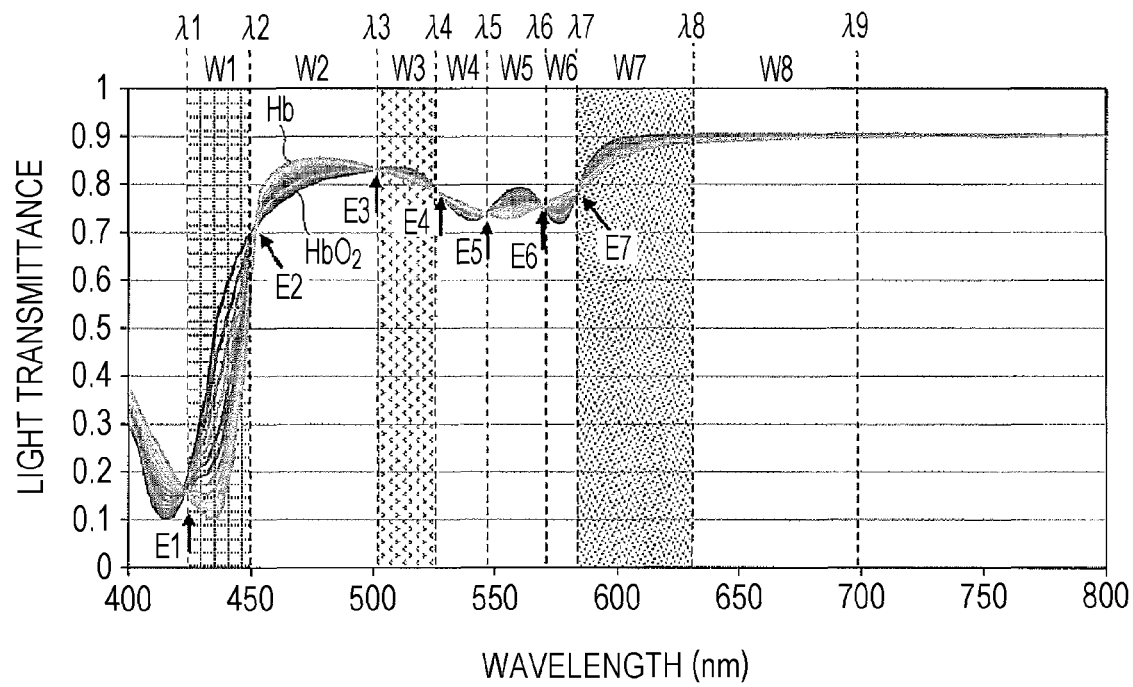
FIG. 3 is a diagram illustrating the spectral characteristics and the wavelength band of a second optical filter used when acquiring a B2 image, a G2 image, and an R2 image.
Figure 4:
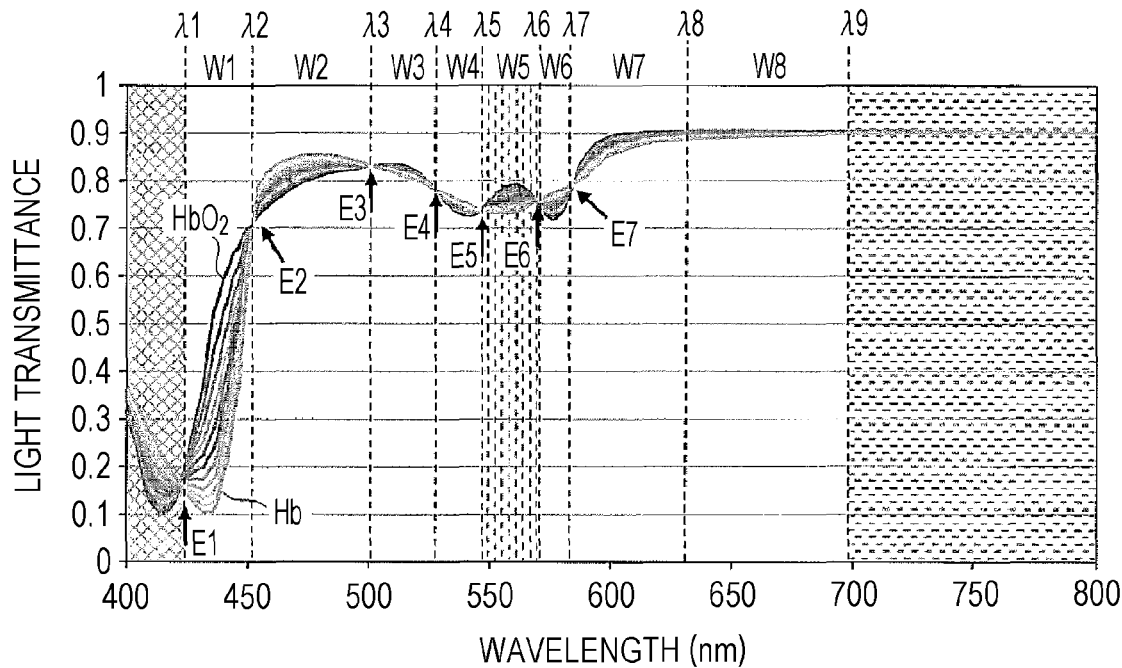
FIG. 4 is a diagram illustrating the spectral characteristics and the wavelength band of a third optical filter used when acquiring a narrowband image (G3 image).

FIGS. 2 to 4 are diagrams illustrating the relationship between the spectral characteristics of biological tissue and the band of the optical filter used in the special observation mode according to this embodiment. FIG. 2 is a diagram illustrating the spectral characteristics and the wavelength band of the first optical filter used when acquiring a wideband image (G1 image). FIG. 3 is a diagram illustrating the spectral characteristics and the wavelength band of the second optical filter used when acquiring the B2 image, the G2 image, and the R2 image. FIG. 4 is a diagram illustrating the spectral characteristics and the wavelength band of the third optical filter used when acquiring the narrowband image (G3 image). The values in the following wavelength bands are expressed with a width of "center wavelength ±3" in consideration of an error that occurs when the optical filter is manufactured. Therefore, it should be noted that the value of the manufacturing error (±3) is an example, and if the error becomes large, the value of the "width" becomes larger. Further, in the following, the reason why the wavelength value at each isosbestic point has a width of ±3 (one example) is that the crossing of spectrums of oxygenated hemoglobin and reduced hemoglobin is gentle.

(i) First Optical Filter (FIG. 2)

The first optical filter is an optical filter that has a first region that transmits light (blue light) having a wavelength of 452±3 to 502±3 nm, a second region that transmits light (green light) having a wavelength of 524±3 to 582±3 nm, and a third region that transmits light (red light) having a wavelength of 630±3 to 700±3 nm.

The first region corresponds to a wavelength band between the transmission spectrum isosbestic point of hemoglobin (a point where the absorption (transmittance) becomes constant regardless of the concentration ratio (oxygen saturation) of each component since the transmission spectrum of hemoglobin is a two-component spectroscopic spectrum in which the sum of the concentrations of oxygenated hemoglobin and reduced hemoglobin becomes constant) E2 (452±3 nm) and the isosbestic point E3 (502±3 nm), and supplies blue light data for generating oxygen saturation information.

The second region corresponds to the wavelength band between an isosbestic point E4 (524±3 nm) and an isosbestic point E7 (582±3 nm). The second region further includes an isosbestic point E5 (546±3 nm) and an isosbestic point E6 (570±3 nm) between the isosbestic point E4 and the isosbestic point E7, and a lot of information on oxygen saturation can be obtained from the image data between the isosbestic points E5 and E6. The third optical filter (FIG. 5) is used to acquire the image data between the isosbestic points E5 and E6.

The third region contains no isosbestic points, has almost no absorption of light (high light transmittance), and provides red light data for generating oxygen saturation information.

(ii) Second Optical Filter (FIG. 3)

The second optical filter is an optical filter that has a fourth region that transmits light (blue light) having a wavelength of 420±3 to 452±3 nm, a fifth region that transmits light (green light) having a wavelength of 502±3 to 524±3 nm, and a sixth region that transmits light (red light) having a wavelength of 582±3 to 615±3 nm.

The fourth region corresponds to a wavelength band between an isosbestic point E1 (420±3 nm) and an isosbestic point E2 (452±3 nm), and provides blue light data for generating oxygen saturation information. The fifth region corresponds to a wavelength band between an isosbestic point E3 (502±3 nm) and an isosbestic point E4 (524±3 nm). The sixth region corresponds to a wavelength band between the isosbestic point E7 (582±3 nm) and the wavelength 630±3 nm.

(iii) Third Optical Filter (FIG. 4)

The third optical filter is an optical filter that has a seventh region that transmits light (blue light) having a wavelength of 380±3 to 420±3 nm, an eighth region that transmits light (green light) having a wavelength of 546±3 to 570±3 nm, and a ninth region that transmits light (red light) having a wavelength of 720±3 to 800±3 nm.

The seventh region corresponds to a wavelength region between the wavelength 380±3 nm and the isosbestic point E1 (420±3 nm), and provides blue light data for generating oxygen saturation information. The eighth region corresponds to a wavelength band between the isosbestic point E5 (546±3 nm) and the isosbestic point E6 (570±3 nm). The ninth region contains no isosbestic points, has almost no absorption of light (high light transmittance), and provides red light data for acquiring deep layer information.

Using the third optical filter makes it possible to acquire image data between the isosbestic points E5 and E6. Since this wavelength band is a band in which the light level of the light source is strong, it is possible to obtain much information regarding the oxygen saturation ($StO_2$). However, when the image data in this wavelength band is used, the dynamic range of the oxygen saturation index value described later is narrow. Therefore, the resolution is low and it may be difficult to accurately obtain the oxygen saturation. In this embodiment, it is proposed to widen the dynamic range of the oxygen saturation index value to improve the resolution and to obtain the oxygen saturation with high accuracy (described later).

(iv) Features at Isosbestic Point

Figure 5:
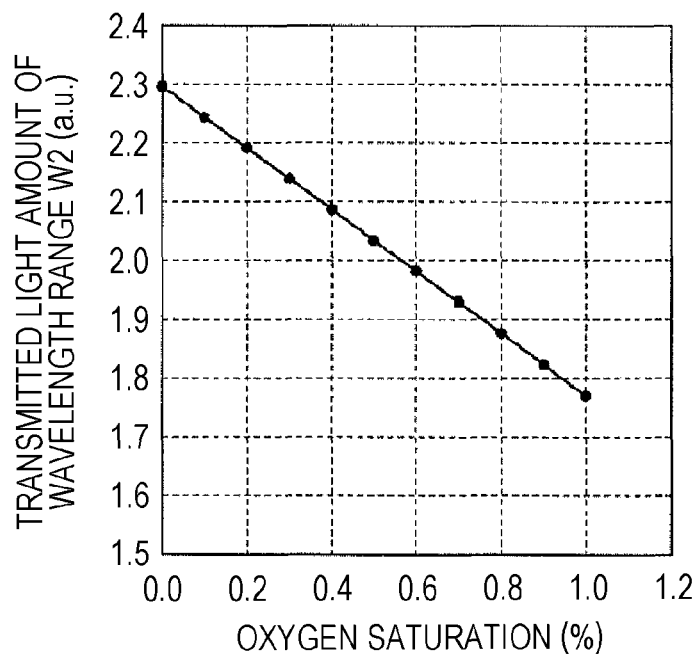
FIG. 5 is a graph plotting the relationship between the amount of transmitted light (vertical axis) of blood and the oxygen saturation (horizontal axis) in a wavelength band W2.

Between adjacent isosbestic points, the absorption monotonically increases or decreases according to the increase in oxygen saturation. Further, between adjacent isosbestic points, absorption A of hemoglobin changes almost linearly with the oxygen saturation. FIG. 5 is a graph plotting the relationship between the amount of transmitted light of blood (vertical axis) and the oxygen saturation (horizontal axis) in the wavelength band W2. The amount of transmitted light on the vertical axis is a value integrated over the entire wavelength band W2. From the graph of FIG. 5, it can be seen that the absorption of hemoglobin decreases linearly with the oxygen saturation in the wavelength band W2. In the adjacent wavelength band W1, the absorption of hemoglobin increases linearly with the oxygen saturation. Specifically, the light transmittance is, exactly saying, the amount of change that complies with the Beer-Lambert Law, but it can be considered to be a substantially linear change in a narrow wavelength region of about 20 nm to 80 nm.

Also, focusing on the wavelength region from the isosbestic point E4 to E7 (that is, the continuous wavelength region of the wavelength bands W4 to W6), the absorption of blood increases monotonically as the oxygen saturation increases in the wavelength bands W4 and W6. However, in the wavelength band W5, conversely, the absorption of blood decreases monotonically as the oxygen saturation increases. However, the inventor has found that the decrease amount of blood absorption in the wavelength band W5 is substantially equal to the sum of the increase amounts of blood absorption in the wavelength bands W4 and W6, and the absorption of blood as a whole in the wavelength band W7 becomes almost constant regardless of the oxygen saturation.

Figure 6:
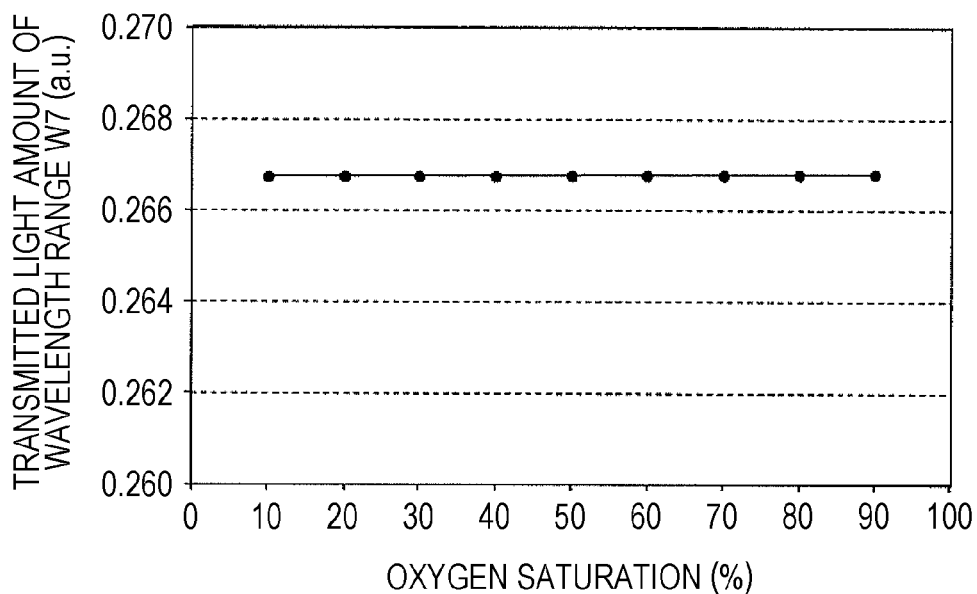
FIG. 6 is a graph plotting the relationship between the amount of transmitted light of blood (vertical axis) and the oxygen saturation (horizontal axis) in wavelength bands W4 to W6.

FIG. 6 is a graph plotting the relationship between the amount of transmitted light of blood (vertical axis) and the oxygen saturation (horizontal axis) in the wavelength bands W4 to W6. The amount of transmitted light on the vertical axis is a value integrated over the entire wavelength bands W4 to W6. The average value of the amount of transmitted light is 0.267 (arbitrary unit), and the standard deviation is $1.86 \times 10^{-5}$. From the graph of FIG. 6, it can be seen that the amount of transmitted light of blood is substantially constant in the entire wavelength bands W4 to W6 regardless of the oxygen saturation.

Further, as illustrated in FIGS. 2 to 4, in the wavelength region of approximately 630±3 nm or more (particularly, 650 nm or more), the hemoglobin absorption is small, and the light transmittance hardly changes even when the oxygen saturation changes. Further, when a xenon lamp is used as the white light source, a sufficiently large amount of light of the white light source can be obtained in a wavelength region of 750±3 nm or less (particularly 720 nm or less). Therefore, for example, a wavelength region of 650±3 to 720±3 nm can be used as a transparent wavelength range where hemoglobin is not absorbed and as a reference wavelength region of the amount of transmitted light. In this specification, a wavelength region from a wavelength of 650±3 nm to a wavelength of 720±3 nm can be defined as a wavelength band WR.

As described above, it is known that absorption $A_{W2}$ of hemoglobin in the wavelength band W2 linearly decreases as the oxygen saturation increases. Since absorption $A_{W4-6}$ of hemoglobin in the wavelength bands W4 to W6 can be regarded as a constant value regardless of the oxygen saturation, the value of absorption Awe based on absorption $A_{W4-6}$ gives an index reflecting the oxygen saturation. Specifically, the oxygen saturation can be represented by an index X defined by the following Expression (1).

$$X = A_{W2} - A_{W4-6} \tag{1}$$

Therefore, the oxygen saturation ($StO_2$) can be estimated from the value of the index X if the quantitative relationship between the oxygen saturation and the index X experimentally or by calculation is obtained previously. As described above, in this embodiment, a device for widening the dynamic range of the oxygen saturation index value to improve the resolution and accurately obtaining the oxygen saturation is devised.

<Example of Internal Configuration of Analysis Processing Unit>

Figure 7:
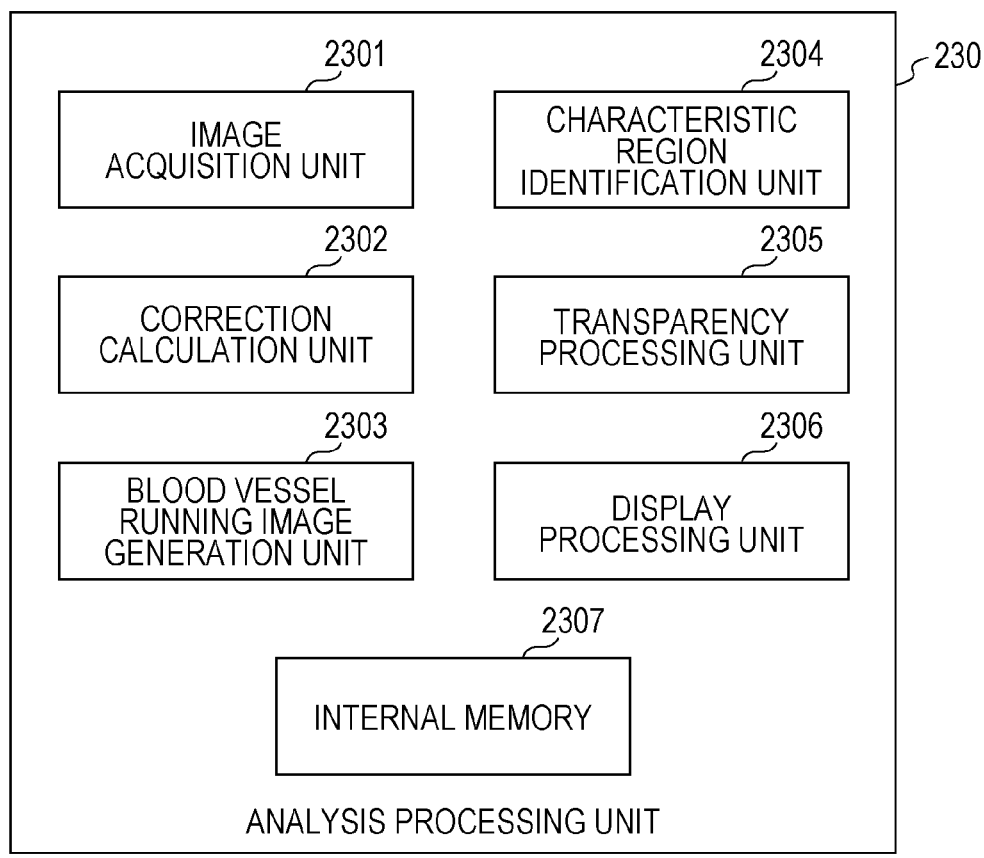
FIG. 7 is a diagram illustrating an internal configuration example of an analysis processing unit 230 according to this embodiment.

FIG. 7 is a diagram illustrating an internal configuration example of the analysis processing unit 230 according to this embodiment. The analysis processing unit 230 includes an image acquisition unit 2301 that acquires the image captured by the electronic scope 100, a correction calculation unit 2302 that corrects the RGB value of the image acquired by the image acquisition unit 2301, a blood vessel running image generation unit 2303 that generates a blood vessel running image using images in each wavelength band corrected by the correction calculation unit 2302, a characteristic region identification processing unit 2304 that calculates a relative hemoglobin concentration and an oxygen saturation, and identifies a characteristic region where the blood concentration is high and the oxygen saturation is low, a transparentization processing unit 2305 that generates an image (blood transparentized image) in which blood is transparentized, a display processing unit 2306 that generates display data for displaying each generated image and related information on the screen of the monitor 300, and an internal memory 2307 that stores parameters and various data and temporarily stores data received from the electronic scope 100. Each processing unit from the image acquisition unit 2301 to the display processing unit 2306 can be configured by a program, for example. In this case, the image processing unit 220 or the analysis processing unit 230 as a processor reads a program for realizing each processing unit from the memory 212 or another storage device (not illustrated in FIG. 1) and expands it in the internal memory 2307, thereby realizing each processing unit. Each processing unit may be configured as a module.

The electronic scope 100 according to this embodiment includes, for example, two or more solid-state image sensors (CMOS image sensors) 108. When capturing an image in the wavelength region corresponding to the first optical filter using it, one solid-state image sensor is used, and when capturing an image in the wavelength region corresponding to the second optical filter using it, another solid-state image sensor is used. The image acquisition unit 2301 acquires an image captured by each solid-state image sensor and transmitted via the driver signal processing unit 110. That is, the image acquisition unit 2301 acquires the B1 image of a wavelength band of 452±3 nm to 502±3 nm, the G1 image of a wavelength band of 524±3 nm to 582±3 nm, and the R1 image of a wavelength band of 630±3 nm to 700±3 nm by the first optical filter. Further, the image acquisition unit 2301, the second optical filter, B2 image of the wavelength region 420±3 nm to 452±3 nm, G2 image of the wavelength band 502±3 nm to 524±3 nm, the wavelength band 582±3 nm Acquire an R2 image of 630±3 nm, from. Further, the image acquisition unit 2301 acquires a correction image (white image) used as a reference when correcting RGB values.

The correction calculation unit 2302 performs, for example, a matrix calculation process in which the correction image acquired by the image acquisition unit 2301 is used to round the RGB value acquired by the on-chip filter in the CMOS image sensor to a numerical value highly correlated with the filter output (for example, a color matrix for color correction, which has a coefficient highly correlated with the wavelength of oxygen saturation is used).

Among the corrected images of the wavelength bands obtained by the correction calculation unit 2302, the blood vessel running image generation unit 2303 uses the B2 image (the image having a wavelength band of 420±3 nm to 452±3 nm) as an image representing a blood vessel in a portion shallow from the surface, the G1 image (the image having a wavelength band of 524±3 nm to 582±3 nm: wideband image) as an image representing a blood vessel of a portion of an intermediate depth from the surface, and the R1 image (the image having a wavelength band of 630±3 nm to 700±3 nm) as an image representing a blood vessel in a portion deep from the surface so as to generate a blood vessel running image.

The characteristic region identification processing unit 2304 calculates the ratio of the B1 image and the G1 image and the Hb (hemoglobin) concentration indicating the blood concentration, and applies them to an oxygen saturation index table prepared in advance (see FIG. 13B) to calculate the oxygen saturation.

The transparentization processing unit 2305 generates an image by using information in a wavelength range in which blood is not absorbed in order to improve a situation in which an inspection (diagnosis) and a surgical site cannot be confirmed by blood. This ensures the visibility of a tissue at the site where bleeding occurs. Specifically, the transparentization processing unit 2305 linearly combines, for each pixel, the G1 image (the image having a wavelength band of 524±3 nm to 582±3 nm), the G2 image (the image having a wavelength band of 502±3 nm to 524±3 nm), the R1 image (the image having a wavelength band of 582±3 nm to 630±3 nm) (a1×the pixel value of the G1 image+a2×the pixel value of the G2 image+a3×the pixel value of the R1 image) so as to generate a blood transparentized image.

The display processing unit 2306 converts each blood vessel running image, the image identifying the characteristic region, and the blood transparentized image into a format that matches the format of the monitor 300 to generate display data, and transmits the display data to the monitor 300.

<Blood Vessel Running Image Generation Process>

Figure 8:
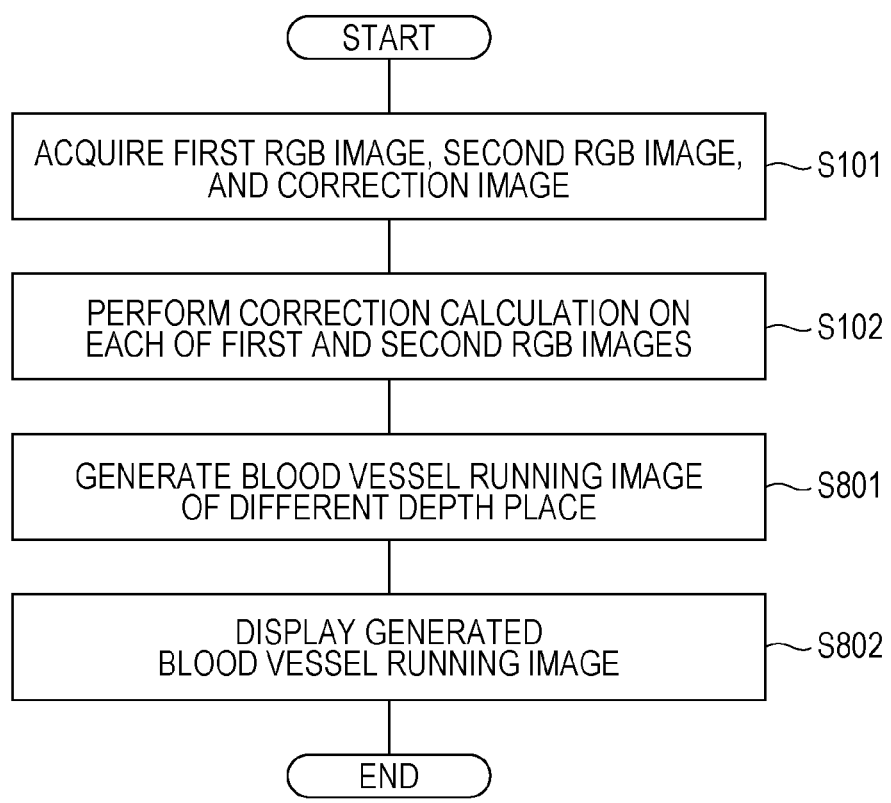
FIG. 8 is a flowchart for explaining a process of generating a blood vessel running image for each depth (blood vessel structure subject: Depth Profile).

FIG. 8 is a flowchart for explaining a process of generating a blood vessel running image for each depth (a blood vessel structure subject: Depth Profile). Here, the operation subject of each step is the image acquisition unit 2301, the correction calculation unit 2302, the blood vessel running image generation unit 2303, and the display processing unit 2306, but when these are realized by a program, the operation subject may be replaced with the analysis processing unit 230 and the image processing unit 220 (hereinafter, also referred to as a processor). In addition, here, as the solid-state image sensor 108, two CMOS image sensors having an on-chip filter are used.

(i) Step 101

The image acquisition unit 2301 acquires a first RGB image, a second RGB image, and a correction image, which are images captured by the electronic scope 100. The first RGB image includes the B1 image having a wavelength band of 452±3 nm to 502±3 nm, the G1 image having a wavelength band of 524±3 nm to 582±3 nm, and the R1 image having a wavelength band of 630±3 nm to 700±3 nm. Further, the second RGB image includes the B2 image having a wavelength region of 420±3 nm to 452±3 nm, the G2 image having a wavelength band of 502±3 nm to 524±3 nm, and the R2 image having a wavelength band of 582±3 nm to 630±3 nm. Further, the correction image is a correction image (white image) used as a reference when correcting each of the RGB values of the first RGB image and the second RGB image.

(ii) Step 102

The correction calculation unit 2302 performs, for example, a matrix calculation process in which the correction image acquired by the image acquisition unit 2301 is used to round the RGB values of the first and second RGB images acquired by the on-chip filter in the CMOS image sensor to a numerical value highly correlated with the filter output (for example, a color matrix for color correction, which has a coefficient highly correlated with the wavelength of oxygen saturation is used). The on-chip filter may not be able to output an appropriate RGB value because there are overlapping wavelength bands. Therefore, the RGB value acquired by the on-chip filter is corrected by a coefficient having a high correlation with the wavelength of oxygen saturation (for example, 3×3 matrix calculation), and proper band separation is realized.

Specifically, as illustrated in FIG. 9, a matrix conversion operation is performed on the RGB value of the on-chip filter (upper part of FIG. 9: (Rs, Gs, Bs)) to generate corrected RGB values (RGB_related_values). In the subsequent process, the corrected RGB value is used as the RGB value.

(iii) Step 801

The blood vessel running image generation unit 2303 generates an image (also called a blood vessel running image: Depth Profile) of a blood vessel at a shallow portion of an observation site of the endoscope, a blood vessel at a deep portion, and a blood vessel at an intermediate position therebetween. This is a process of generating an image by utilizing the fact that the visible information in the depth direction differs depending on the observation wavelength. A short-wavelength image is used to obtain information on blood vessels and tissues near the surface of the observation site, and is used to obtain information on blood vessels and tissues located deeper from the surface of the observation site as the wavelength becomes longer. In Step 801, these pieces of information are visualized to generate information on the relative depth of blood vessels.

When observing a tissue with the light having a short wavelength, the light is saturated at a shallow portion from the surface of the observation site. Therefore, information on a deep portion (for example, blood vessel data) is lost, and information on a shallow portion (blood vessel information) is selectively observed. Therefore, by displaying the B2 image obtained by irradiating the light having a wavelength band of 420±3 nm to 452±3 nm, the state (running state) of the blood vessel at the shallow portion of the observation site can be confirmed. In addition, it is possible to generate a blood vessel image of a shallow portion from the surface of the observation site by using the B1 image.

When observing a tissue with light of a medium wavelength, the light is saturated at a place with a medium depth from the surface of the observation site. For this reason, information on deep places (for example, blood vessel data) is lost, and information on places with medium depth (blood vessel information) is selectively observed. Therefore, by displaying the G1 image obtained by irradiating the light having a wavelength band 524±3 nm to 582±3 nm, the state (running state) of blood vessels at the medium depth of the observation site can be confirmed.

When observing a tissue with long-wavelength light, the light reaches a deeper portion from the surface of the observation site. Therefore, it becomes possible to selectively observe information (blood vessel information) at a deep portion from the surface of the observation site. Therefore, by displaying the R1 image obtained by irradiating the light having a wavelength band of 630±3 nm to 700±3 nm, the state (running state) of the blood vessel at a position deeper that the observation site can be confirmed.

(iv) Step 802

The display processing unit 2306 converts each of the B2 image, the G1 image, and the R1 image into a format used when displaying the image on the monitor 300, and transmits the converted data to the monitor 300. The monitor 300 receives data corresponding to the B2 image, the G1 image, and the R1 image from the display processing unit 2306 of the analysis processing unit 230, and displays each image on the screen.

<Example of Blood Vessel Running Image>

Figure 10:
FIGS. 10A-10D are diagrams illustrating an example of a blood vessel running image of an observation site generated by a blood vessel running image generation process (FIG. 8).
Figure 10:
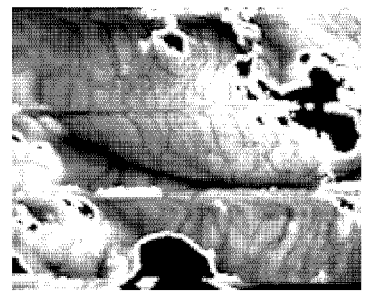
Figure 10:
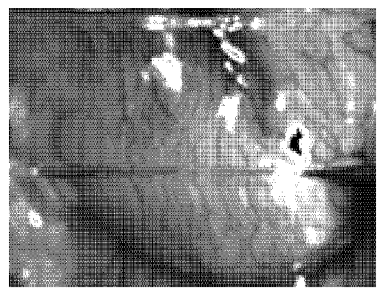
Figure 10:

FIG. 10 is a diagram illustrating an example of a blood vessel running image of an observation site generated by the blood vessel running image generation process (FIG. 8). FIG. 10A illustrates an example of a visible light image of an observation site. FIG. 10B is diagram illustrating the B2 image (the image obtained by irradiating light with a wavelength band of 420±3 nm to 452±3 nm), and illustrating an image example of the state of a blood vessel at a shallow portion from the surface of the observation site. FIG. 10C is a diagram illustrating the G1 image (the image obtained by irradiating light with a wavelength band 524±3 nm to 582±3 nm), and illustrating an image example of the state of a blood vessel at a medium depth from the surface of the observation site. FIG. 10D is a diagram illustrating the R1 image (the image obtained by irradiating light with a wavelength band of 630±3 nm to 700±3 nm), and illustrating an image example of the state of a blood vessel at a position deeper than the surface of the observation site.

As described above, by generating the B2 image, the G1 image, and the R1 image, it is possible to acquire the profile of each depth at the observation site, and to inspect and diagnose the object effectively and efficiently.

<Characteristic Region Identifying Process>

Figure 11:
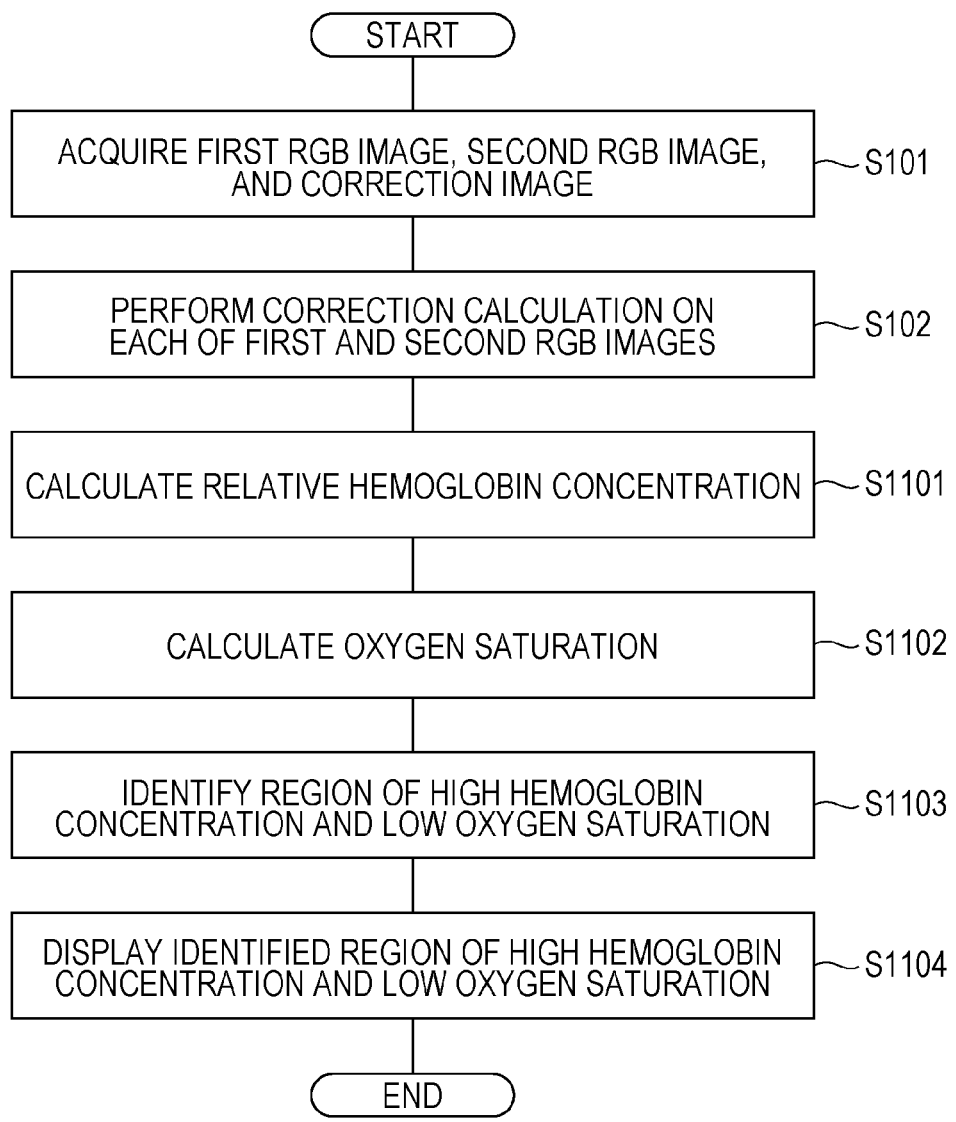
FIG. 11 is a flowchart for explaining details of a characteristic region identifying process according to this embodiment.

FIG. 11 is a flowchart for explaining details of the characteristic region identifying process according to this embodiment. Here, the operation subject of each step is the image acquisition unit 2301, the correction calculation unit 2302, the characteristic region identification processing unit 2304, and the display processing unit 2306, but when these are realized by a program, the operation subject may be replaced with the analysis processing unit 230 and the image processing unit 220 (hereinafter, also referred to as a processor). In addition, here, as the solid-state image sensor 108, two CMOS image sensors having an on-chip filter are used. Note that Steps 101 and 102 are the same as those in FIG. 8, so description thereof will be omitted.

(i) Step 1101

The characteristic region identification processing unit 2304 calculates the relative hemoglobin concentration at the observation site. The hemoglobin concentration (blood concentration) is obtained by calculating the ratio of each element as oxygenated hemoglobin, reduced hemoglobin, and scattered light as the elements included in the spectral information of the mucous membrane. In the absence of scattered light, as illustrated in FIG. 12A, the baseline becomes almost horizontal, so the relative hemoglobin concentration (blood concentration) can be represented by the displacement Hb=G1/R1 from the baseline to G1 (wide) (R1 represents the baseline). However, since the element of scattered light actually enters, as illustrated in FIG. 12B, the baseline is not horizontal and has an inclination (the baseline becomes dull). The spectral characteristic of scattering can be represented by a combination of ordinary spectral characteristics of RGB as illustrated in FIG. 12C. Therefore, the relative hemoglobin concentration in consideration of scattered light can be calculated by linearly combining RGB to reproduce the spectral characteristics as the baseline. Expression (2) is an equation used when calculating the relative hemoglobin concentration in consideration of scattered light. It can be seen that, in Expression (2), the optimum coefficients $\alpha$, $\beta$, and $\gamma$ (that can reproduce the spectral characteristics) may be determined. Since the baseline having the slope in the spectral characteristic of FIG. 12B can be reproduced only from G1 and R1, $\alpha=0$ and $\beta=\gamma=1$ can be set in the example of FIG. 12B (FIG. 12C).

[Math. 1]

$$Hbcnc' = \frac{G1(\text{wide})}{\alpha * B1 + \beta * G1 + \gamma * R1} \qquad (2)$$

By performing the above calculation, the characteristic region identification processing unit 2304 can calculate the relative hemoglobin concentration at each location of the observation site.

(ii) Step 1102

The characteristic region identification processing unit 2304 calculates the oxygen saturation. When obtaining the oxygen saturation, the characteristic region identification processing unit 2304 calculates B1/G1, and the value of the relative Hb concentration calculated in Step 901 and the value of B1/G1 are fitted to the oxygen saturation calculation table prepared in advance (FIG. 13B), and checks what percentage of oxygen saturation the point represented by a pair of Hb concentration and B1/G1 corresponds to. Thereby, the oxygen saturation can be obtained.

Conventionally, the oxygen saturation has been obtained by the point represented by the pair of Hb concentration and G1/G3, but as illustrated in FIG. 13A, when the Hb concentration is low, the resolution of characteristics is not good from 0% to 100% of the oxygen saturation. Therefore, when G1/G3 as in the conventional case is used, the oxygen saturation cannot be calculated accurately. On the other hand, in this embodiment, since B1/G1 is used, as illustrated in FIG. 13B, the resolution of characteristics from 0% to 100% of the oxygen saturation is improved. Therefore, if B1/G1 is used, the oxygen saturation can be accurately obtained.

(iii) Step 1103

The characteristic region identification processing unit 2304 identifies a place in the observation site where the relative hemoglobin concentration (blood concentration) is a predetermined Hb value or more, and the oxygen saturation is a predetermined percentage or less, on the basis of the relative hemoglobin concentration and the oxygen saturation obtained in Steps 1101 and 1102.

Identifying a place where the relative hemoglobin concentration (blood concentration) is a predetermined Hb value or more and the oxygen saturation is a predetermined percentage or less means, for example, specifying a place affected by cancer. Many new blood vessels are created at a cancer place, and the blood vessels carry nutrients and oxygen to the cancer cells, so that the cancer cells grow steadily. Therefore, at the cancer place, the blood flow is high (the blood concentration is high) and the oxygen consumption is high, so the oxygen saturation is low. Therefore, by identifying a place with high blood flow and low oxygen content, a place that may be affected by cancer can be identified, and the efficiency of cancer diagnosis (cancer detection) can be improved.

Then, the characteristic region identification processing unit 2304 generates an observation site image indicating a high blood concentration (high Hb concentration) place in red and yellow (a red place has a higher concentration), a place with low oxygen saturation in light blue, and an observation site image indicating a place with high blood concentration (high Hb concentration) and low oxygen saturation in yellow.

(iv) Step 1104

The display processing unit 2306 converts each of the characteristic region image of the observation site generated in Step 1103 into a format used when displaying the image on the monitor 300, and transmits the converted data to the monitor 300. The monitor 300 receives data corresponding to each characteristic region image from the display processing unit 2306 of the analysis processing unit 230, and displays each characteristic region image on the screen.

<Example of Characteristic Region Image>

Figure 14:
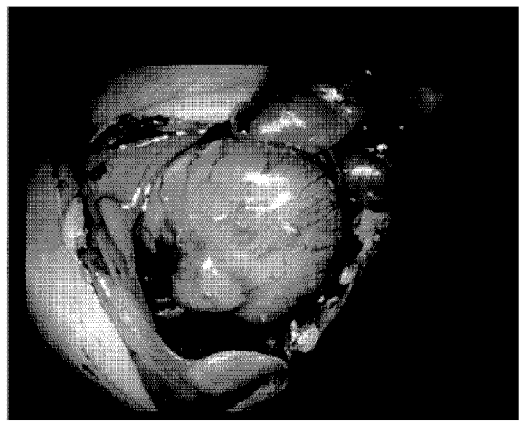
FIGS. 14A-14D are diagrams illustrating an example of each characteristic region image of the observation site, which is generated by the characteristic region identifying process (FIG. 11).
Figure 14:
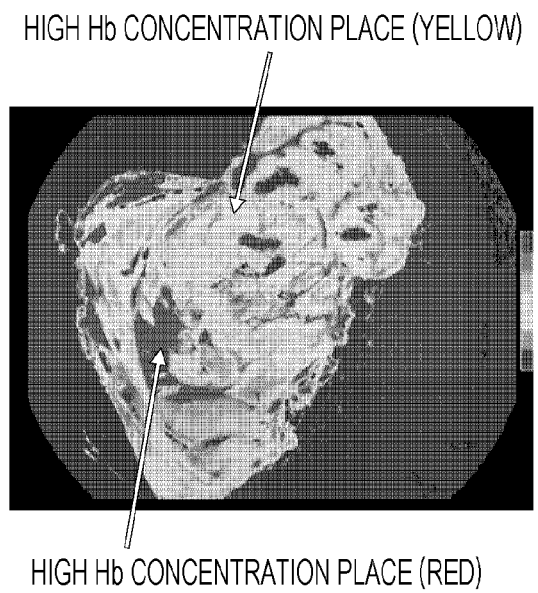
Figure 14:
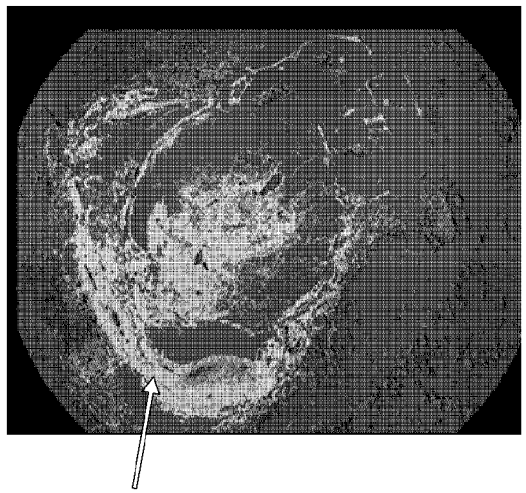
Figure 14:
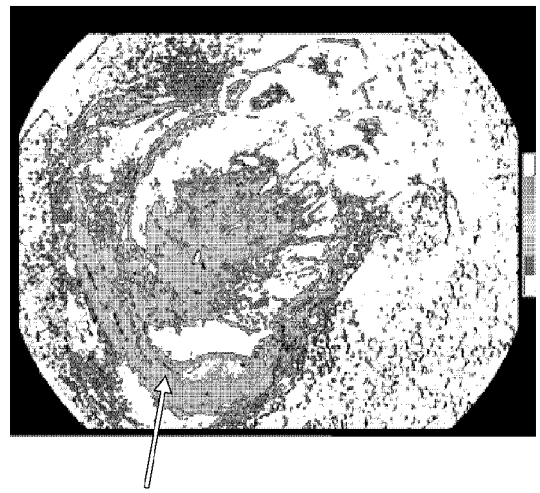

FIG. 14 is a diagram illustrating an example of each characteristic region image of the observation site generated by the characteristic region identifying process (FIG. 11). FIG. 14A illustrates an example of a visible light image of the observation site. FIG. 14B illustrates an image example of a portion where the blood concentration (Hb concentration) is a predetermined Hb value or more (a portion with a large blood flow) in the observation site. FIG. 14C illustrates an image example of a portion where the oxygen saturation is a predetermined percentage or less (a portion where the oxygen consumption is large) in the observation site. FIG. 14D illustrates an image example of a portion where the blood concentration (Hb concentration) is a predetermined Hb value or more and the oxygen saturation is a predetermined percentage (a place where the blood flow is large but the oxygen amount is low) in the observation site.

As described above, by the characteristic region identifying process according to this embodiment, each characteristic region in the observation site (for example, three types: a place with a large amount of blood flow, a place with a large amount of oxygen consumption, and a place with a large amount of blood flow but a small amount of oxygen) can be accurately identified, and each region can be displayed on the display screen, so that an endoscope operator such as a doctor can efficiently make a diagnosis/consultation. By generating the B2 image, the G1 image, and the R1 image, it is possible to acquire the profile of each depth at the observation site, and it is possible to effectively and efficiently examine and diagnose the object.

<Transparentizing Process>

Figure 15:
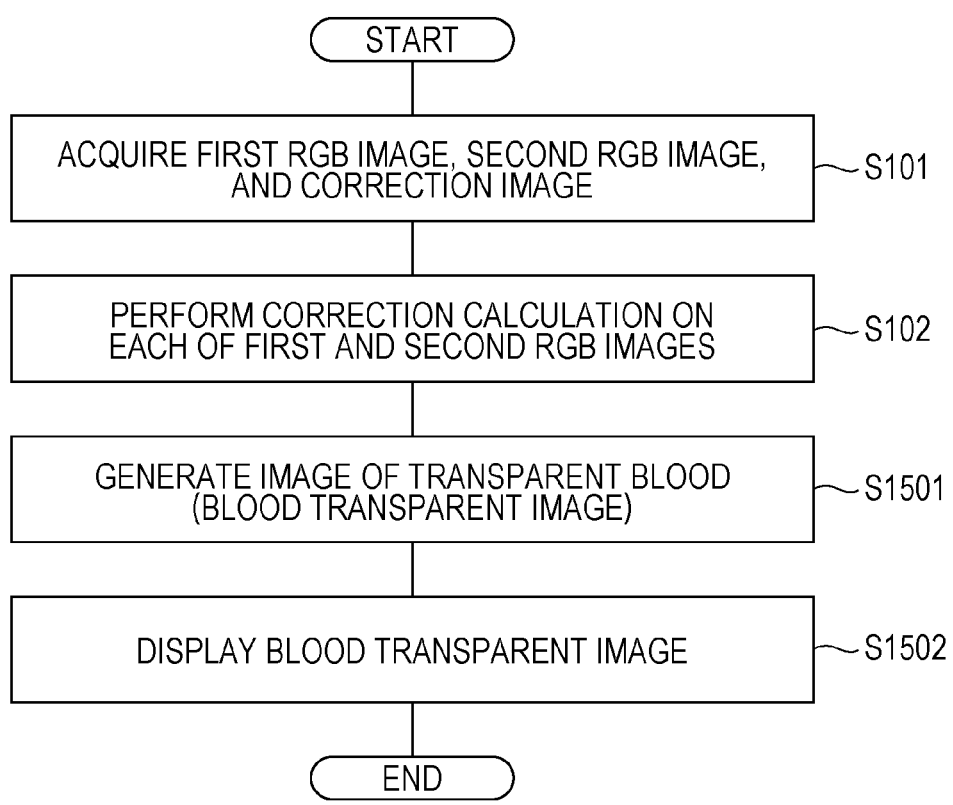
FIG. 15 is a flowchart for explaining details of a blood transparentizing process according to this embodiment.

FIG. 15 is a flowchart for explaining details of the blood transparentizing process according to this embodiment. Here, the operation subject of each step is the image acquisition unit 2301, the correction calculation unit 2302, the transparentization processing unit 2305, and the display processing unit 2306, but when these are realized by a program, the operation subject may be replaced with the analysis processing unit 230 and the image processing unit 220 (hereinafter, also referred to as a processor). In addition, here, as the solid-state image sensor 108, two CMOS image sensors having an on-chip filter are used. Note that Steps 101 and 102 are the same as those in FIG. 8, so description thereof will be omitted.

The blood transparentizing process creates a display image of the observation site using information in the wavelength range in which there is no absorption of blood, thereby ensuring the visibility of the tissue and allowing the procedure involving bleeding to proceed.

(i) Step 1501

The transparentization processing unit 2305 generates an image (blood transparentized image) in which blood is transparentized by assigning image data (values obtained by correcting the imaged data in Step 102) to B_Channel, G_Chennel, and R_Channel, respectively. Normally, the input signal of each region of RGB is output in the color of the same area. That is, B_Channel (blue) is assigned to the B image having a wavelength band of 425±3 nm to 452±3 nm, G_Chennel (green) is assigned to the G image having a wavelength band of 500±3 nm to 525±3 nm, and R_Channel (red) is assigned to the R image having a wavelength band of 600±3 nm to 630±3 nm. In this case, since blood is expressed in red, it has been pointed out that the visibility of the observation site deteriorates.

On the other hand, in this embodiment, the transparentization processing unit 2305 outputs the input signal of each wavelength region in a color of a different wavelength region. Specifically, the transparentization processing unit 2305 assigns the G2 image having a wavelength band of 502±3 nm to 524±3 nm to B_Channel (blue), the R2 image having a wavelength band of 582±3 nm to 630±3 nm to G_Channel, and the R1 image having a wavelength band of 630±3 nm to 700±3 nm to R_Channel as it is. The output value in the G_Chennel of the G1 image having a wavelength band of 524±3 nm to 582±3 nm is adjusted (by multiplying the G1 image by the subtraction parameter (0.05 to 0.5) to linearly combine other images) to generate a blood transparentized image.

(ii) Step 1502

The display processing unit 2306 converts the blood transparentized image of the observation site generated in Step 1501 into a format used when displaying the image on the monitor 300, and transmits the converted data to the monitor 300. The monitor 300 receives data corresponding to the blood transparentized image from the display processing unit 2306 of the analysis processing unit 230, and displays the blood transparentized image on the screen.

<Example of Blood Transparentized Image>

Figure 16:
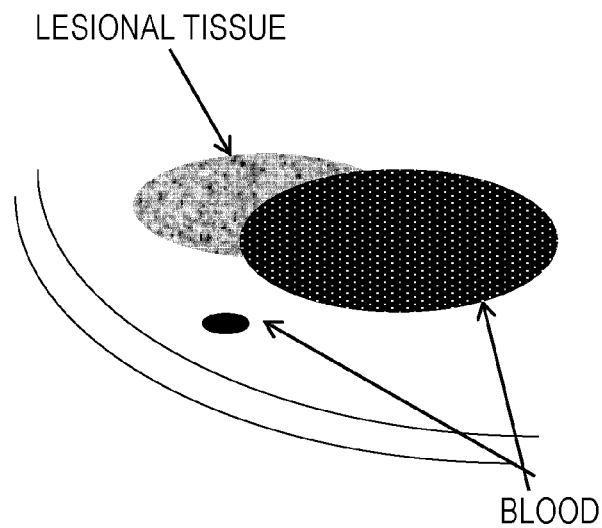
FIG. 16 is a diagram illustrating an example of a blood transparentized image obtained by the blood transparentizing process.
Figure 16:
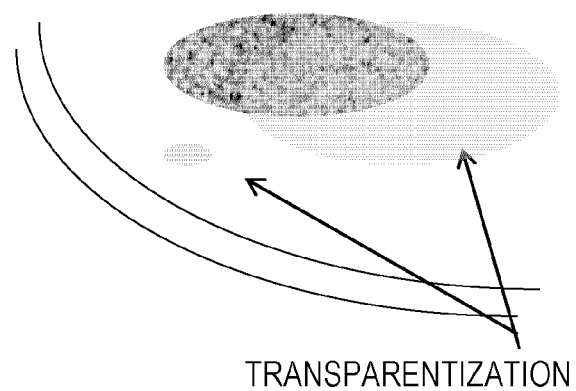
Figure 16:
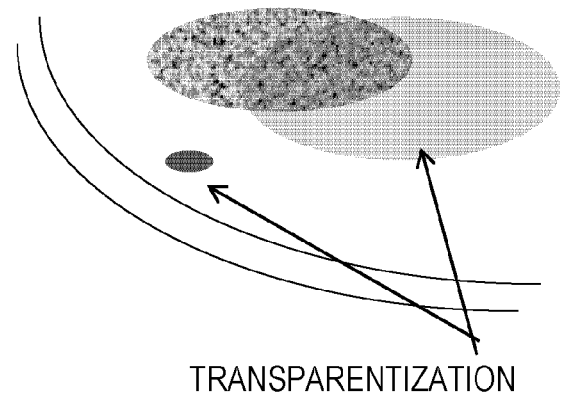
Figure 16:
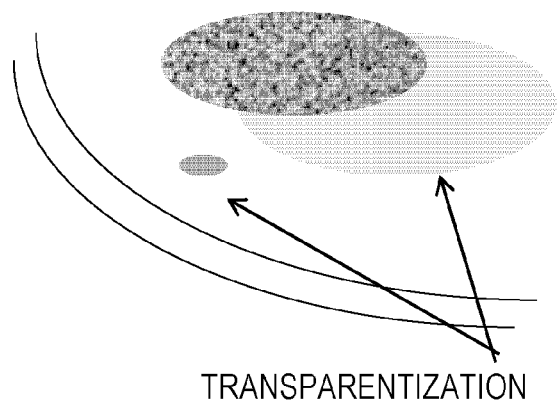

FIG. 16 is a diagram illustrating an example of a blood transparentized image obtained by the blood transparentizing process. FIG. 16A illustrates an example of a normal RGB output image of the observation site. FIG. 16B illustrates an example of the blood transparentized image (which can be set to −0.2, for example) when the subtraction parameter of the G1 image is set. FIG. 16C illustrates an example of the blood transparentized image when the subtraction parameter of the G1 image is set to 0. FIG. 16D illustrates an example of the blood transparentized image when another subtraction parameter of the G1 image is set (an example when the subtraction parameter is further increased: generally, it can be set to −0.5).

As illustrated in FIG. 16B, the image signal derived from blood becomes very weak, the blood becomes transparent, and the colors at other places are reproduced naturally.

In FIG. 16C, the subtraction of the G1 image is set to 0 times. In this case, the image information of blood becomes small, but some remains.

FIG. 16D illustrates a blood transparentized image when the G1 image is subtracted excessively, but a region that is originally displayed in white by further subtracting the G1 image greatly (for example, it can be set to 0.5 times subtraction) and becomes reddish.

As described above, in the blood transparentizing process according to this embodiment, data in six wavelength bands (B1 image, G1 image, R1 image, B2 image, G2 image, and R2 image) is used (in DRI, data of three wavelength bands are used). Further, since the G1 image is multiplied by the parameter coefficient and subtracted, the blood image information can be reduced, and the output image can be finely adjusted. Therefore, it is possible to absorb the color difference of the on-chip filters of the plurality of solid-state image sensors (CMOS image sensors).

Further, in this embodiment, information other than the blood transparentized image (such as the blood vessel running image and the characteristic region image) can be acquired at the same time based on the data in the six wavelength bands. Therefore, it is not necessary to execute the time series switching process according to the type of image to be acquired.

MODIFICATIONS (1) First Modification

In the above embodiment, an example in which the first to third optical filters are arranged on the light source side has been illustrated, but the present invention is not limited to this, and the first to third filters may be arranged on the imaging unit side.

Figure 17:
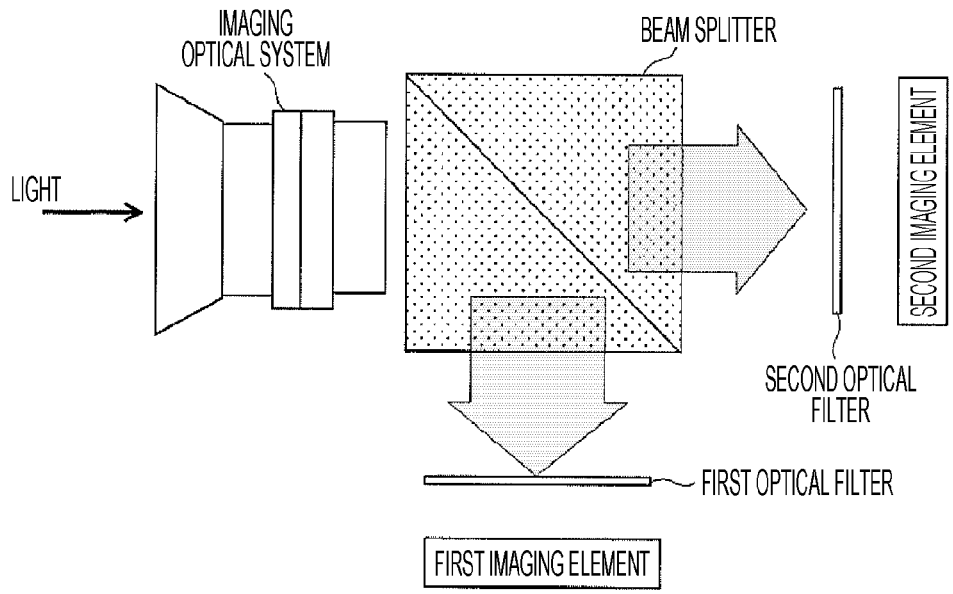
FIG. 17 is a diagram illustrating an example in which first and second image sensors (first and second solid-state image sensors: for example, CMOS sensor) are arranged in first and second filters.

FIG. 17 illustrates an example in which the first and second filters and the first and second image sensors (first and second solid-state image sensors: for example, CMOS sensor) are arranged. The light incident on the camera lens is imaged by the imaging optical system and then divided into two, and passes through the first optical filter and the second optical filter, respectively, and the first image sensor and the second image sensor respectively acquire the first RGB image (B1 image, G1 image, and R1 image) and the second RGB image (B2 image, G2 image, and R2 image) described above. By doing this, the first and second RGB images can be acquired at the same time in real time, so there is no delay in image acquisition and calculation even when using the six wavelength bands, and there is no image shift. Note that the imaging optical system may be arranged behind the beam splitter as long as it is on the optical path (the same applies to the following modifications).

(2) Second Modification

Figure 18:
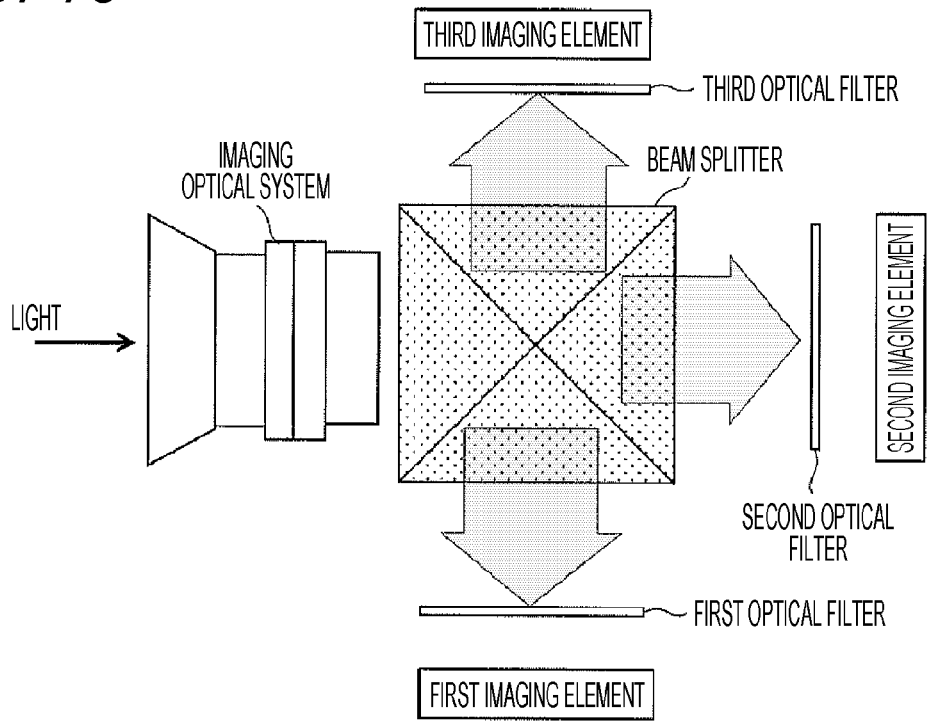
FIG. 18 is a diagram illustrating an example in which a third filter and a third image sensor (third solid-state image sensor: for example, CMOS sensor) that images light that has passed through the third filter are arranged.

FIG. 18 is a diagram illustrating an example in which the third filter and the third image sensor (third solid-state image sensor: CMOS sensor, for example) that picks up light that has passed through the third filter are arranged. Also in this case, similarly, since three types of RGB images can be simultaneously acquired in real time, there is no delay in image acquisition and calculation using nine wavelength bands, and no image shift occurs.

(3) Third Modification

Figure 19:
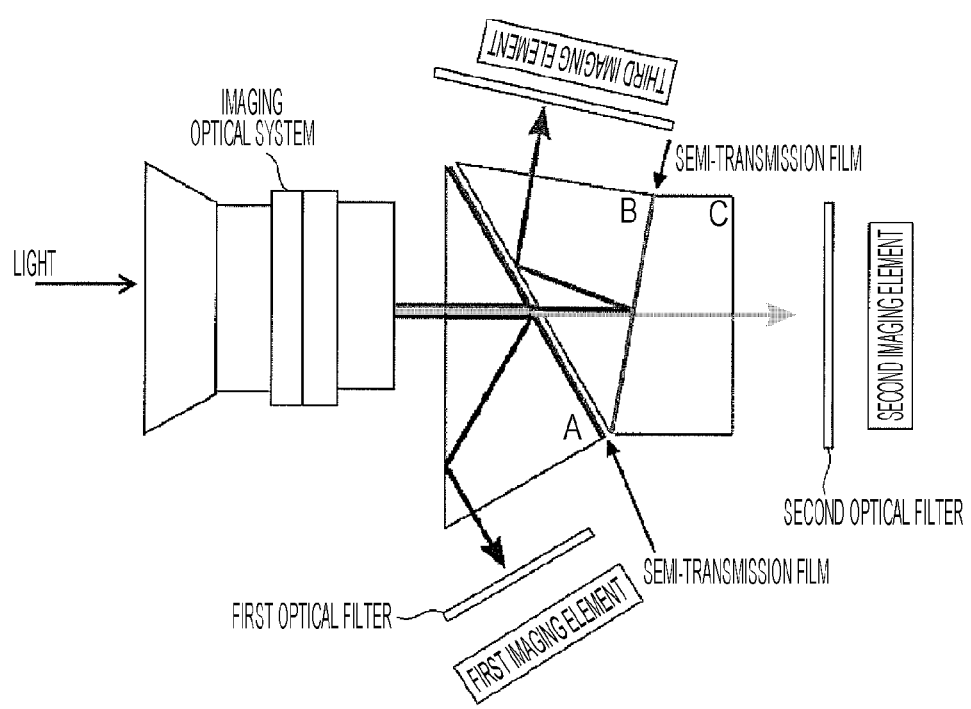
FIG. 19 is a diagram illustrating an example in which a three-plate prism is used instead of a beam splitter.

FIG. 19 is a diagram illustrating an example in which a three-plate prism is used instead of the beam splitter. In the three-plate prism, the interface of the prism is composed of dichroic mirrors, and the amount of light in the image is divided into three by simple semi-transmission. The function and configuration of the image sensor are similar to those illustrated in FIGS. 17 and 18. The advantage of using the three-plate prism is that it is easy to implement because it can be used with minor changes to the existing configuration of the three-plate image sensor camera.

(4) Fourth Modification

FIG. 20 is a diagram illustrating the third optical filter (FIG. 20A: corresponding to the optical filter illustrated in FIG. 4) for acquiring a narrowband image (an image formed by light having a wavelength of 546±3 to 570±3 nm) and the first optical filter (FIG. 20B: corresponding to the optical filter illustrated in FIG. 2) for acquiring a wideband image (an image formed by light having a wavelength of 524±3 nm to 582±3 nm). The narrowband image and the wideband image are used to calculate the degree of change in the spectral characteristic of the biological tissue (curve of characteristic: feature of spectral characteristic) at the place C illustrated in FIG. 20B. The degree of change in the spectral characteristics of the biological tissue can be obtained by dividing the wideband image by the narrowband image (wideband image/narrowband image). Since this value is the amount of change affected by the blood concentration and the oxygen saturation, it is necessary to perform conversion based on the blood concentration when obtaining the oxygen saturation index value from this degree of change. It should be noted that when the degree of change is large, the oxygen saturation is high, and when the degree of change is small, the oxygen saturation is low.

Figure 21:
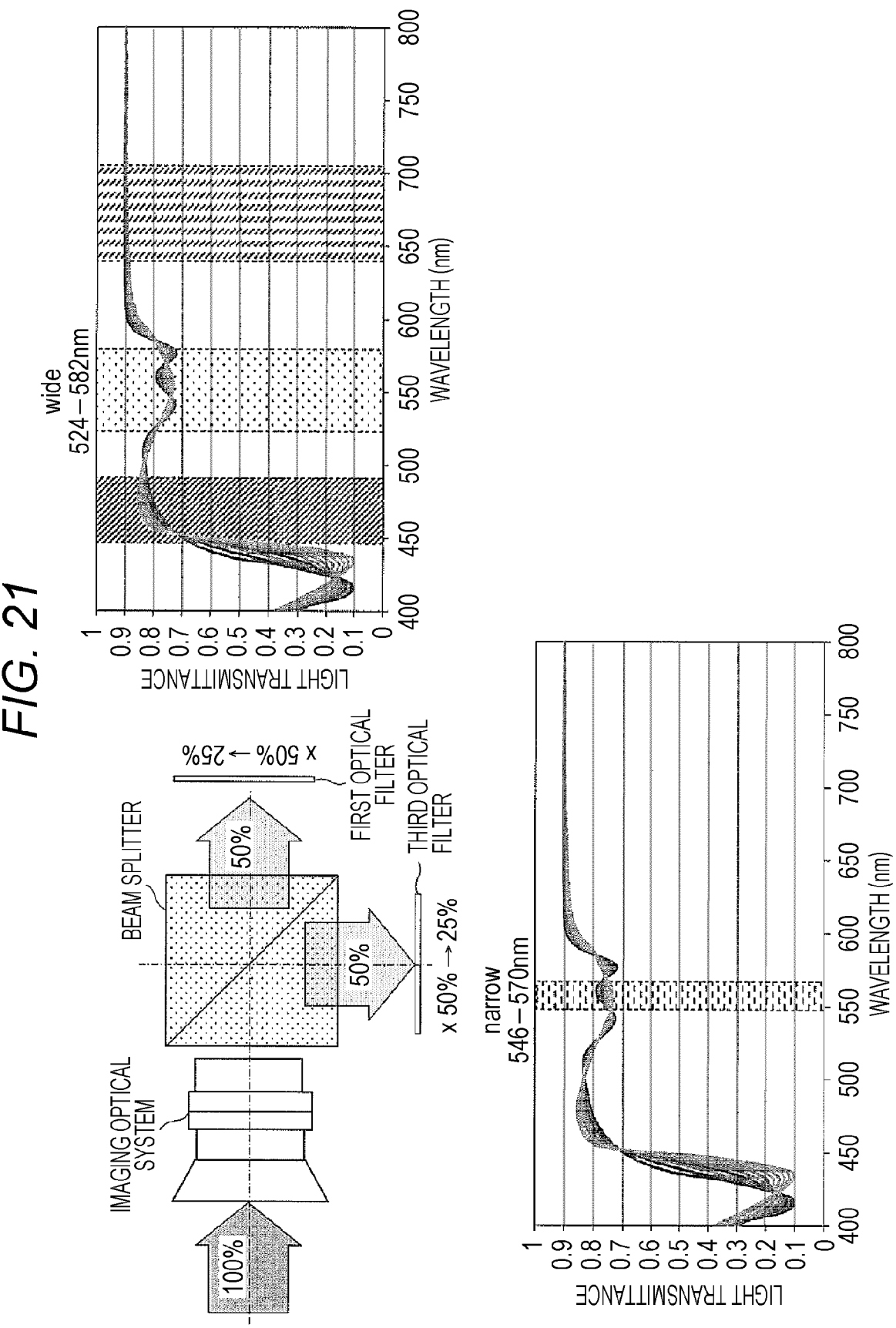
FIG. 21 is a diagram for explaining that, when the light emitted from the light source is split by the beam splitter, the amount of light is reduced to about 25% at the stage of being incident on each image sensor.

The wideband image and the narrowband image can be acquired by using the third optical filter (FIG. 20A) and the first optical filter (FIG. 20B) in the arrangement example (FIG. 17) of the filter and the image sensor illustrated in the first modification. However, in the configuration example of FIG. 17, the amount of light becomes 50% by the beam splitter (for example, the beam splitter that splits the light into 50%), and further becomes 50% by each optical filter. That is, as can be seen from FIG. 21, which illustrates the relationship between the emitted light (100% light amount) and the light whose amount is reduced by the beam splitter and each optical filter, the amount of light emitted from the light source becomes about 25% at the stage of being incident on each image sensor. In this case, the wavelength band for acquiring the narrowband image (546±3 nm to 570±3 nm, which is a band of 24±6 nm) is equal to or less than half of the wavelength band (524±3 nm to 582±3 nm, which is a band of 58±6 nm) for acquiring the wideband image. Therefore, the narrowband image becomes a darker image than the wideband image. If the above calculation (wideband image/narrowband image) is executed as it is, the calculation accuracy will be affected. In this respect, since the configuration according to the first modification uses two image sensors, it is not necessary to acquire images at the same exposure time. Therefore, by setting the exposure time of the image sensor for capturing the narrowband image longer than the exposure time of the image sensor for capturing the wideband image, it is possible to eliminate the light amount difference due to the difference in the wavelength band. For example, the exposure time of the image sensor that captures the narrowband image may be set to 2 to 2.5 times the exposure time of the image sensor that captures the wideband image. Note that the exposure time of the image sensor that captures the narrowband image is, for example, set to twice the exposure time of the image sensor that captures the wideband image in the initial setting, and may be optimized after actually acquiring the narrowband image and the wideband image.

(5) Fifth Modification

Figure 22:
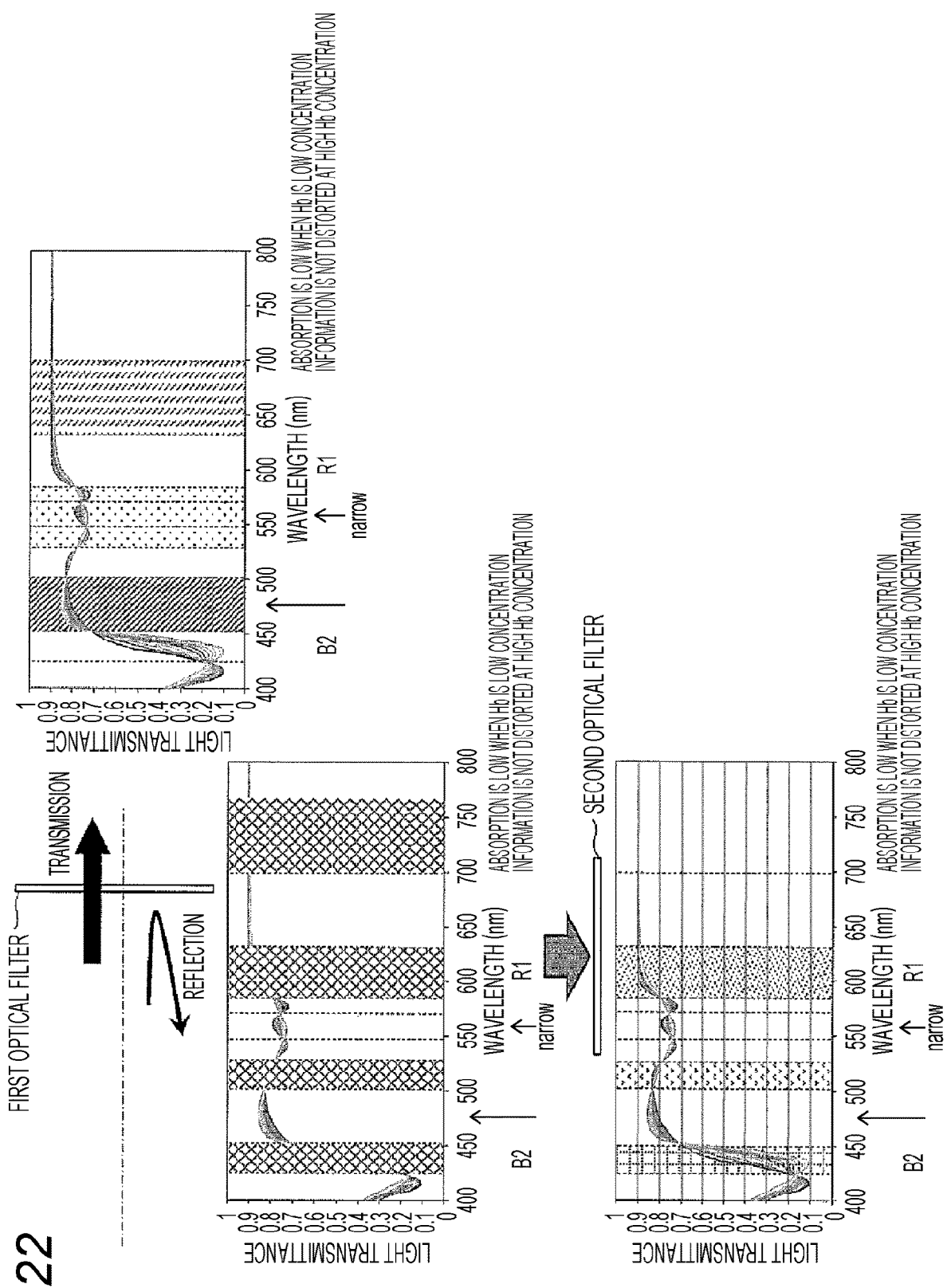
FIG. 22 is a diagram for explaining the principle of a fifth modification.

A fifth modification proposes an arrangement example of the optical filter and two image sensors when using the first optical filter (see FIG. 2) and the second optical filter (see FIG. 3) having the wavelength bands in a complementary relationship to each other. FIG. 22 is a diagram for explaining the principle of the fifth modification, and FIG. 23 is a diagram illustrating a configuration example of an optical element according to the fifth modification.

The optical filter (for example, the first optical filter (see FIG. 2)) is obtained by depositing, for example, dozens of thin films on layers (for example, 60-layer deposition) to achieve desired filter characteristics. The inventor has verified about what would happen in light which did not pass through the first optical filter. Then, it has been initially thought that the light would be absorbed by the vapor deposition film of the first optical filter, but as illustrated in FIG. 22, it has been found that all the light that do not pass through is reflected by the first optical filter. Therefore, the inventor has devised to form a layer of a desired optical filter (for example, the first optical filter (FIG. 2)) instead of the split film of the beam splitter.

Figure 23:
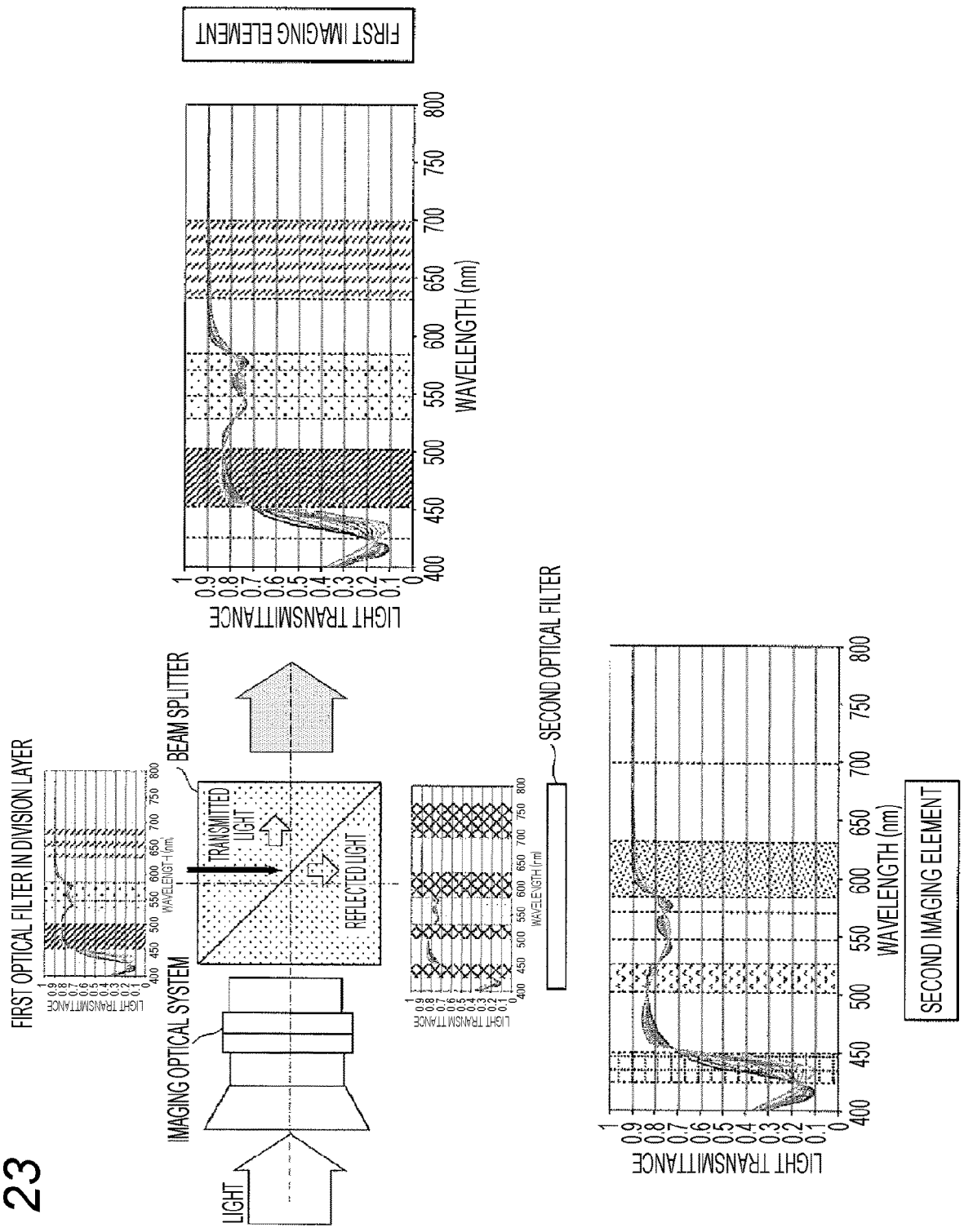
FIG. 23 is a diagram illustrating a configuration example of an optical element according to the fifth modification.

That is, as illustrated in FIG. 23, the arrangement configuration of the optical elements includes a beam splitter that includes the first optical filter (FIGS. 2 and 20B) as a splitting film, a first image sensor (for example, CMOS sensor) that captures light (light passed through the first optical filter) passed through the beam splitter, the second optical filter (see FIG. 3: having characteristics of passing the light of 420±3 nm to 452±3 nm, the light of 502±3 nm to 524±3 nm light, and the light of 582±3 nm to 630±3 nm) that filters the light reflected on the beam splitter (the light having a wavelength band other than the light passed through the first optical filter), and a second image sensor (for example, CMOS sensor) that captures light passed through the second optical filter. By adopting such a configuration, each calculation (for example, oxygen saturation calculation, blood vessel running image generation process, blood transparentizing process, etc.) can be executed using the light of which the wavelength bands have the complementary relationship without splitting and reducing the light by the beam splitter to 50%.

(6) In the first to fifth modifications, the reflected light from the biological tissue is divided by optical elements such as a beam splitter and a prism and made incident on each image sensor, but the arrangement configuration of these optical elements may be provided at a place near the operation unit or inside the processor 200 instead of the tip of the electronic scope 100 (in FIG. 1, the image sensor 108 is arranged in the tip of the electronic scope 100). In this case, the reflected light from the tip of the endoscope 100 is guided to an optical element such as a beam splitter or a prism by an optical fiber or the like.

SUMMARY OF EMBODIMENTS (1) As described above, in this embodiment, the lights of R of the RGB light (first wavelength band (630±3 nm to 700±3 nm)) such that the wavelength band of light is nested, G of the second wavelength band (524±3 nm to 582±3 nm), B of the third wavelength band (452±3 nm to 502±3 nm), R of the fourth wavelength band (582±3 nm to 630±3 nm), G of the fifth wavelength band (from 502±3 nm to 524±3 nm), and B of the sixth wavelength band (420±3 nm to 452±3 nm) are irradiated to the biological tissue to acquire images, these images are subjected to a predetermined image processing to generate images, and the generated images are displayed. However, the second wavelength band, the third wavelength band, the fifth wavelength band, and the sixth wavelength band are defined with the boundaries of the bands by the wavelength of the isosbestic point where the transmittance becomes constant regardless of the oxygen saturation. Then, the G1 image data corresponding to the second wavelength band, and in addition to the G1 image data, at least one of the R1 image data corresponding to the first wavelength band other than the G1 image data, the B1 image data corresponding to the third wavelength band, the R2 image data corresponding to the fourth wavelength band, the G2 image data corresponding to the fifth wavelength band, and the B2 image data corresponding to the sixth wavelength band are used to perform the image processing, so that a special optical image is generated. By doing so, the image quality of the special optical image can be improved.

Specifically, the B2 image data is used to generate a first blood vessel image at a first depth position (shallow position) from the surface of the biological tissue, and the G1 image data is used to generate a second blood vessel image at a second depth position (intermediate depth position) deeper than the first depth, and the R1 image data is used to generate a third blood vessel image at a third depth position (deepest position) deeper than the second depth. In this way, it is possible to generate an image corresponding to various applications by utilizing the characteristics of each acquired image to generate an image.

When obtaining the oxygen saturation, conventionally, a value obtained by dividing the image obtained by irradiating the G1 image with light having a wavelength band of 546±3 nm to 570±3 nm has been used, but in this embodiment, the value of B1 image data/G1 image data is used. By doing so, the resolution of the oxygen saturation index value (table) can be improved, so that the oxygen saturation of the biological tissue can be accurately obtained (see FIG. 13). By dividing the G1 image data by the linear combination of the B1 image data, the G1 image data, and the R1 image data, it becomes possible to calculate the relative hemoglobin concentration without the influence of scattered light.

Further, a place satisfying a characteristic condition that the hemoglobin concentration is equal to or higher than a first threshold value, and the oxygen saturation is less than a second threshold value may be identified in the biological tissue. A characteristic image taking a display form in which the place satisfying the characteristic condition is distinguished from other places may be generated, and the characteristic image may be displayed on the screen. By doing so, it is possible to identify a place where the cancer cells are likely to be active (a place where the cancer is likely to be affected), and to further examine that place. Therefore, the object can be accurately diagnosed.

Further, the endoscope system according to this embodiment assigns the G2 image data to the blue wavelength region, and assigns the R2 image data to the green wavelength region, so that the level of image data derived from blood adhered to the surface of the biological tissue can be reduced. Therefore, it is possible to generate a blood transparentized image in which blood is made transparent. By displaying this blood transparentized image on the screen, even if the operator has a bleeding site in the biological tissue of the object, it is possible to continue the treatment with a good visibility.

The endoscope system according to this embodiment may include at least the first image sensor that generates the R1 image data, the G1 image data, and the B1 image data, and the second image sensor that generates the R2 image data, the G2 image data, and the B2 image data.

Further, in this embodiment, the light of each wavelength band is generated using a filter, but the present invention is not limited to this, and the image data (R1 to B2 image data) of the wavelength bands may be acquired using a laser light source device (LED light source device) that emits light of each wavelength band without using a filter.

Further, a special image may be generated by further using each RGB image data obtained by irradiating light of each wavelength band obtained by the third optical filter (FIG. 4). By doing so, it becomes possible to provide a wider variety of observation modes.

(2) According to this embodiment (fourth modification), the degree of change in the spectral characteristic of the biological tissue in a narrowband (the degree of bending of the characteristic) is calculated by the image based on the wideband light and the image based on the narrowband light, and outputted. At this time, since there is a light amount difference between the narrowband light and the wideband light (narrowband light is darker), a difference is set in the exposure time of the two image sensors (CMOS sensors). That is, the exposure time of the image sensor for capturing the narrowband light is set to be longer than the exposure time of the image sensor for capturing the wideband light (about 2 to 2.5 times). By doing so, it is possible to reduce the calculation error due to the light amount difference existing between the narrowband light and the wideband light. The wideband light is light having a wavelength band of 524±3 nm to 582±3 nm, and the narrowband light is light having a wavelength band of 546±3 nm to 570±3 nm.

(3) According to this embodiment (fifth modification), in the optical element (beam splitter), a layer of an optical filter (the first optical filter (see FIG. 2)) is provided instead of the beam splitting film. In this case, the reflected light from the biological tissue caused by irradiating the biological tissue with the illumination light is divided, and a first wavelength band light which is the light of a predetermined wavelength band group (the light of 452±3 nm to 502±3 nm, the light of 524±3 nm to 582±3 nm, and the light of 630±3 nm to 700±3 nm) is transmitted through the layer of the optical filter. On the other hand, a second wavelength band light which is the light of a wavelength group other than the predetermined wavelength band group (the light of 400±3 nm to 452±3 nm, the light of 502±3 nm to 524±3 nm, and the light of 582±3 nm to 630±3 nm) is reflected by the layer of the optical filter. Then, a first imaging unit (CMOS sensor) generates first image data based on a first wavelength band light, and a second imaging unit (another CMOS sensor) generates second image data based on the second wavelength band light. Furthermore, an image processing unit executes a predetermined image process (for example, oxygen saturation calculation, blood vessel running image generation process, blood transparentizing process, etc.) based on the first image data and the second image data. The image processing result is displayed on the display screen of the monitor 300.

SPECIFIC MATTERS OF THE PRESENT DISCLOSURE (1) Specific Matter 1

An endoscope system capable of operating in a normal observation mode for irradiating a biological tissue with white light to acquire an image and a special observation mode for irradiating a biological tissue with light of a specific wavelength band to acquire an image, comprising:

an illumination unit that irradiates a biological tissue with illumination light including at least R of a first wavelength band, G of a second wavelength band, B of a third wavelength band, R of a fourth wavelength band, G of a fifth wavelength band, and B of a sixth wavelength band;

an imaging unit that generates image data based on reflected light from the biological tissue generated by irradiating the biological tissue with the illumination light;

an image processing unit that acquires the image data from the imaging unit and performs a predetermined image process; and a display unit that displays an image generated by the predetermined image process of the image processing unit on a screen, wherein at least the second wavelength band, the third wavelength band, the fifth wavelength band, and the sixth wavelength band are defined with boundaries therebetween by a wavelength at an isosbestic point at which transmittance becomes constant regardless of oxygen saturation, the second wavelength band includes within the band an isosbestic point other than the isosbestic point which is the boundary of the band, the sixth wavelength band is a shorter wavelength band than the third wavelength band, the fifth wavelength band is a shorter wavelength band than the second wavelength band, the fourth wavelength band is a shorter wavelength band than the first wavelength band, the image data includes R1 image data corresponding to R light of the first wavelength band, G1 image data corresponding to G light of the second wavelength band, B1 image data corresponding to B light of the third wavelength band, R2 image data corresponding to R light of the fourth wavelength band, G2 image data corresponding to G light of the fifth wavelength band, and B2 image data corresponding to B light of the sixth wavelength band, and the image processing unit generates a special light image by performing an image process using the G1 image data and at least one of the R1 image data, the B1 image data, the R2 image data, the G2 image data, and the B2 image data other than the G1 image data.

(2) Specific Matter 2

The endoscope system according to specific matter 1, wherein
the first wavelength band is 630±3 nm to 700±3 nm,
the second wavelength band is 524±3 nm to 582±3 nm,
the third wavelength band is 452±3 nm to 502±3 nm,
the fourth wavelength band is 582±3 nm to 630±3 nm,
The fifth wavelength band is 502±3 nm to 524±3 nm,
the sixth wavelength band is from 420±3 nm to 452±3 nm, and
452±3 nm, 502±3 nm, 524±3 nm, and 582±3 nm are wavelengths of the isosbestic point.

(3) Specific Matter 3

The endoscope system according to specific matter 1 or 2, wherein the image processing unit performs
a process of generating a first blood vessel image at a first depth position from a surface of the biological tissue using the B2 image data,
a process of generating a second blood vessel image at a second depth position deeper than the first depth using the G1 image data,
a process of generating a third blood vessel image at a third depth position deeper than the second depth using the R1 image data.

(4) Specific Matter 4

The endoscope system according to any one of specific matters 1 to 3,
wherein the image processing unit calculates a hemoglobin concentration indicating a blood concentration by dividing the G1 image data by at least the R1 image data, and obtains an oxygen saturation of the biological tissue based on a value of the hemoglobin concentration and a value of the B1 image data/the G1 image data.

(5) Specific Matter 5

The endoscope system according to specific matter 4,
wherein the image processing unit identifies, in the biological tissue, a place which satisfies a characteristic condition that the hemoglobin concentration is equal to or more than a first threshold and the oxygen saturation is less than a second threshold, and generates a characteristic image of the place satisfying the characteristic condition to take a display form distinguished from other places, and
the display unit displays the characteristic image on a screen.

(6) Specific Matter 6

The endoscope system according to specific matter 4 or 5,
wherein the image processing unit divides the G1 image data by a linear combination of the B1 image data, the G1 image data, and the R1 image data to calculate a relative hemoglobin concentration with the influence of scattered light removed, and obtains the oxygen saturation using the relative hemoglobin concentration.

(7) Specific Matter 7

The endoscope system according to any one of specific matters 1 to 6,
wherein the image processing unit assigns the G2 image data to a blue wavelength region, and assigns the R2 image data to a green wavelength region to lower a level of image data derived from blood attached to a surface of the biological tissue so as to generate a blood transparentized image in which the blood is transparent, and the display unit displays the blood transparentized image on a screen.

(8) Specific Matter 8

The endoscope system according to specific matter 7,
wherein the image processing unit further multiplies the G1 image data by a predetermined subtraction parameter, and linearly combines the G2 image data assigned to the blue wavelength region, the R2 image data assigned to the green wavelength region, and the G1 image data multiplied by the subtraction parameter to generate the blood transparentized image.

(9) Specific Matter 9

The endoscope system according to any one of specific matters 1 to 8,
wherein the imaging unit includes a first image sensor that generates the R1 image data, the G1 image data, and the B1 image data, and a second image sensor that generates the R2 image data, the G2 image data, and the B2 image data.

(10) Specific Matter 10

An endoscope system capable of operating in a normal observation mode for irradiating a biological tissue with white light to acquire an image and a special observation mode for irradiating a biological tissue with light of a specific wavelength band to acquire an image, comprising:
an illumination unit that irradiates a biological tissue with illumination light;
an optical element that divides reflected light from the biological tissue generated by irradiating the biological tissue with the illumination light, and outputs at least a first reflected light and a second reflected light;
a first optical filter that transmits light of a wavelength band of a first group in the first reflected light;
a second optical filter that transmits light of a wavelength band of a second group containing a part of wavelength band of the first group;
a first imaging unit that generates first image data corresponding to light of a predetermined wavelength band based on light of the wavelength band of the first group;
a second imaging unit that generates second image data corresponding to light of a wavelength band, which is contained in the predetermined wavelength band and narrower than the predetermined band, based on light of the wavelength band of the second group;
an image processing unit that calculates a feature of a spectral characteristic of the biological tissue in the wavelength band narrower than the predetermined wavelength band by dividing the first image data by the second image data; and
an output unit that outputs a calculation result of the image processing unit,
wherein an exposure time of the second imaging unit is set to be longer than an exposure time of the first imaging unit.

(11) Specific Matter 11

The endoscope system according to specific matter 10,
wherein the first image data is wideband image data corresponding to light having a wavelength band of 524±3 nm to 582±3 nm, and
the second image data is narrowband image data corresponding to light having a wavelength band of 546±3 nm to 570±3 nm.

(12) Specific Matter 12

The endoscope system according to specific matter 10 or 11,
wherein the image processing unit calculates a degree of change in a spectral characteristic of the biological tissue in a range from 546±3 nm to 570±3 nm.

(13) Specific Matter 13

The endoscope system according to any one of specific matters 10 to 12,
wherein an exposure time of the second imaging unit is set to be twice or longer than an exposure time of the first imaging unit.

(14) Specific Matter 14

An endo scope system capable of operating in a normal observation mode for irradiating a biological tissue with white light to obtain an image and a special observation mode for irradiating a biological tissue with light of a specific wavelength band to obtain an image, comprising:
an illumination unit that irradiates the biological tissue with illumination light;
an optical element that includes a layer of an optical filter instead of a beam splitting film, transmits a first wavelength band light, which is light of a predetermined wavelength band group in the reflected light from the biological tissue generated by irradiating the biological tissue with the illumination light, through a layer of the optical filter, reflects a second wavelength band light, which is light of a wavelength group other than the predetermined wavelength band group on a layer of the optical filter, and outputs the first wavelength band light and the second wavelength band light;
a first imaging unit that generates first image data corresponding to light of the predetermined wavelength band group based on the first wavelength band light;
a second imaging unit that generates second image data corresponding to light of a wavelength group other than the predetermined wavelength band group based on the second wavelength band light;
an image processing unit that performs predetermined image processing based on the first image data and the second image data; and
an output unit that outputs a calculation result of the image processing unit.

(15) Specific Matter 15

The endoscope system according to specific matter 14,
wherein the first wavelength band light and the second wavelength band light are lights having a complementary relationship with respect to a wavelength group.

(16) Specific Matter 16

The endoscope system according to specific matter 14 or 15,
wherein the optical filter has a characteristic of transmitting light of 452±3 nm to 502±3 nm, light of 524±3 nm to 582±3 nm, and light of 630±3 nm to 700±3 nm.

(17) Specific Matter 17

The endoscope system according to specific matter 14, further comprising:
a correction optical filter that transmits a part of the second wavelength band light,
wherein the second imaging unit generates the second image data based on the light that has been transmitted through the correction optical filter.

(18) Specific Matter 18

The endoscope system according to specific matter 17,
wherein the correction optical filter has a characteristic of transmitting light of 420±3 nm to 452±3 nm, light of 502±3 nm to 524±3 nm, and light of 582±3 nm to 630±3 nm.

(19) Specific Matter 19

A method for operating an endoscope system in a special observation mode in which light of a specific wavelength band is irradiated to a biological tissue to acquire an image, comprising:
irradiating, by an illumination unit, a biological tissue with illumination light containing at least light of R of a first wavelength band, G of a second wavelength band, B of a third wavelength band, R of a fourth wavelength band, G of a fifth wavelength band, and B of a sixth wavelength band;
generating, by an imaging unit, image data based on reflected light from the biological tissue generated by irradiating the biological tissue with the illumination light;
acquiring, by an image processing unit, the image data from the imaging unit and performing predetermined image processing; and
displaying, by a display unit, an image generated by the predetermined image processing of the image processing unit on a screen,
wherein at least the second wavelength band, the third wavelength band, the fifth wavelength band, and the sixth wavelength band are defined with boundaries between bands by a wavelength of an isosbestic point at which transmittance becomes constant regardless of oxygen saturation,
the second wavelength band includes an isosbestic point other than the isosbestic point that becomes a boundary of bands, the sixth wavelength band is a wavelength band shorter than the third wavelength band, the fifth wavelength band is a wavelength band shorter than the second wavelength band, and the fourth wavelength band is a wavelength band shorter than the first wavelength band,
the image data includes R1 image data corresponding to light of R of the first wavelength band, G1 image data corresponding to light of G of the second wavelength band, B1 image data corresponding to light of B of the third wavelength band, R2 image data corresponding to light of R of the fourth wavelength band, G2 image data corresponding to light of G of the fifth wavelength band, and B2 image data corresponding to light of B of the sixth wavelength band, and
when the image data is generated, the image processing unit generates a special light image by performing an image process using the G1 image data and at least one of the R1 image data other than the G1 image data, the B1 image data, the R2 image data, the G2 image data, and the B2 image data.

(20) Specific Matter 20

The method according to specific matter 19, wherein
the first wavelength band is 630±3 nm to 700±3 nm,
the second wavelength band is 524±3 nm to 582±3 nm,
the third wavelength band is 452±3 nm to 502±3 nm,
the fourth wavelength band is 582±3 nm to 630±3 nm,
The fifth wavelength band is 502±3 nm to 524±3 nm,
the sixth wavelength band is from 420±3 nm to 452±3 nm, and
452±3 nm, 502±3 nm, 524±3 nm, and 582±3 nm are wavelengths of the isosbestic point.

(21) Specific Matter 21

The method according to specific matter 19 or 20,
wherein the performing of the predetermined image processing by the image processing unit includes
generating, by the image processing unit, a first blood vessel image at a first depth position from a surface of the biological tissue using the B2 image data,
generating, by the image processing unit, a second blood vessel image at a second depth position deeper than the first depth using the G1 image data, and
generating, by the image processing unit, a third blood vessel image at a third depth position deeper than the second depth using the R1 image data.

(22) Specific Matter 22

The method according to any one of specific matters 19 to 21,
wherein the performing of the predetermined image processing by the image processing unit includes
calculating, by the image processing unit, a hemoglobin concentration indicating a blood concentration by dividing the G1 image data by at least the R1 image data, and
obtaining, by the image processing unit, an oxygen saturation of the biological tissue based on a value of the hemoglobin concentration and a value of the B1 image data/the G1 image data.

(23) Specific Matter 23

The method according to specific matter 22,
wherein the performing of the predetermined image processing by the image processing unit includes
identifying, by the image processing unit, a place satisfying a characteristic condition that the hemoglobin concentration is equal to or more than a first threshold in the biological tissue, and the oxygen saturation is less than a second threshold, and
generating, by the image processing unit, a characteristic image that takes a display form in which the place satisfying the characteristic condition is distinguished from other places, and
the display unit displays the characteristic image on a screen.

(24) Specific Matter 24

The method according to specific matter 22 or 23,
wherein the image processing unit divides the G1 image data by a linear combination of the B1 image data, the G1 image data, and the R1 image data to calculate a relative hemoglobin concentration with the influence of scattered light removed, and obtains the oxygen saturation using the relative hemoglobin concentration.

(25) Specific Matter 25

The method according to any one of specific matters 19 to 24,
wherein the performing of the predetermined image processing by the image processing unit includes
assigning, by the image processing unit, the G2 image data to a blue wavelength region, and assigning the R2 image data to a green wavelength region to lower a level of image data derived from blood attached to a surface of the biological tissue so as to generate a blood transparentized image in which the blood is transparent, and
the display unit displays the blood transparentized image on a screen.

(26) Specific Matter 26

The method according to specific matter 25,
wherein the performing of the predetermined image processing by the image processing unit includes
multiplying, by the image processing unit, the G1 image data by a predetermined subtraction parameter, and linearly combining the G2 image data assigned to the blue wavelength region, the R2 image data assigned to the green wavelength region, and the G1 image data multiplied by the subtraction parameter to generate the blood transparentized image.

(27) Specific Matter 27

The method according to any one of specific matters 19 to 26,
wherein the imaging unit includes a first image sensor and a second image sensor, and
the first image sensor generates the R1 image data, the G1 image data, and the B1 image data, and the second image sensor generates the R2 image data, the G2 image data, and the B2 image data.

REFERENCE SIGNS LIST 1 endoscope system
100 electronic scope
108 solid-state image sensor
110 driver signal processing unit
200 processor
202 system controller
204 timing controller
208 lamp
220 image processing unit
230 analysis processing unit
260 optical filter device
262 optical filter
264 filter drive unit
300 monitor
2301 image acquisition unit
2302 correction calculation unit 2303 blood vessel running image generation unit
2304 characteristic region identifying process
2306 display processing unit
2307 internal memory

The invention claimed is:

1. An endoscope system capable of operating in a normal observation mode for irradiating a biological tissue with white light to acquire a first image and a special observation mode for irradiating the biological tissue with light of a specific wavelength band to acquire a second image, comprising:
- a lamp that irradiates the biological tissue with illumination light including at least red light R1 of a first wavelength band, green light G1 of a second wavelength band, blue light B1 of a third wavelength band, red light R2 of a fourth wavelength band, green light G2 of a fifth wavelength band, and blue light B2 of a sixth wavelength band;
- an image sensor that generates image data based on reflected light from the biological tissue generated by irradiating the biological tissue with the illumination light, the image data including a first RGB image, a second RGB image different from the first RGB image, and a correction image;
- an image processor that acquires the image data including the first RGB image, the second RGB image, and the correction image from the image sensor and performs a predetermined image process; and
- a display that displays a special light image generated by the predetermined image process of the image processor on a screen, wherein:
at least the second wavelength band, the third wavelength band, the fifth wavelength band, and the sixth wavelength band are defined with boundaries therebetween,
the boundaries are wavelengths at isosbestic points at which transmittance becomes constant regardless of oxygen saturation,
the second wavelength band includes isosbestic points other than the isosbestic points,
the first RGB image of the image data includes R1 image data corresponding to R1 of the first wavelength band, G1 image data corresponding to G1 of the second wavelength band, and B1 image data corresponding to B1 of the third wavelength band,
the second RGB image of the image data includes R2 image data corresponding to R2 of the fourth wavelength band, G2 image data corresponding to G2 of the fifth wavelength band, and B2 image data corresponding to B2 of the sixth wavelength band,
the correction image is used as a reference when the image processor corrects RGB values of the first RGB image and the second RGB image,
the image processor generates the special light image by performing an image process using the G1 image data and at least one of the R1 image data, the B1 image data, the R2 image data, the G2 image data, and the B2 image data,
the first wavelength band is 630±3 nm to 700±3 nm,
the second wavelength band is 524±3 nm to 582±3 nm,
the third wavelength band is 452±3 nm to 502±3 nm,
the fourth wavelength band is 582±3 nm to 630±3 nm,
the fifth wavelength band is 502±3 nm to 524±3 nm,
the sixth wavelength band is from 420±3 nm to 452±3 nm,
452±3 nm, 502±3 nm, 524±3 nm, and 582±3 nm are wavelengths at the isosbestic points,
the image processor assigns the G2 image data to a blue wavelength region, and assigns the R2 image data to a green wavelength region to generate a blood transparentized image in which the blood is transparent,
the image processor multiplies the G1 image data by a predetermined subtraction parameter coefficient, and
the display displays the blood transparentized image on the screen.

2. The endoscope system according to claim 1,
wherein the image processor performs
a process of generating a first blood vessel image at a first depth position from a surface of the biological tissue using the B2 image data,
a process of generating a second blood vessel image at a second depth position deeper than the first depth position using the G1 image data, and
a process of generating a third blood vessel image at a third depth position deeper than the second depth position using the R1 image data.

3. The endoscope system according to claim 1,
wherein the image processor calculates a hemoglobin concentration indicating a blood concentration by dividing the G1 image data by the R1 image data, and obtains an oxygen saturation of the biological tissue based on a value of the hemoglobin concentration and a ratio of the B1 image data and the G1 image data.

4. The endoscope system according to claim 3,
wherein the image processor identifies, in the biological tissue, a place which satisfies a characteristic condition that the hemoglobin concentration is equal to or more than a first threshold and the oxygen saturation is less than a second threshold, and generates a characteristic image of the place satisfying the characteristic condition to take a display form distinguished from other places, and
the display displays the characteristic image on the screen.

5. The endoscope system according to claim 3,
wherein the image processor divides the G1 image data by a linear combination of the B1 image data, the G1 image data, and the R1 image data to calculate a relative hemoglobin concentration with the influence of scattered light removed, and obtains the oxygen saturation using the relative hemoglobin concentration.

6. The endoscope system according to claim 1,
wherein the image processor further linearly combines the G2 image data assigned to the blue wavelength region, the R2 image data assigned to the green wavelength region, and the G1 image data multiplied by the subtraction parameter to generate the blood transparentized image.

7. The endoscope system according to claim 1,
wherein the image sensor includes a first image sensor that generates the R1 image data, the G1 image data, and the B1 image data, and a second image sensor that generates the R2 image data, the G2 image data, and the B2 image data.

* * * * *